(12) United States Patent
Everett et al.

(10) Patent No.: US 7,456,957 B2
(45) Date of Patent: Nov. 25, 2008

(54) LITTROW SPECTROMETER AND A SPECTRAL DOMAIN OPTICAL COHERENCE TOMOGRAPHY SYSTEM WITH A LITTROW SPECTROMETER

(75) Inventors: Matthew J. Everett, Livermore, CA (US); Yan Zhou, Pleasanton, CA (US); Jochen M. M. Horn, San Francisco, CA (US); Keith O'Hara, Pleasanton, CA (US); James P. Foley, Fremont, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 252 days.

(21) Appl. No.: 11/196,043

(22) Filed: Aug. 3, 2005

(65) Prior Publication Data

US 2007/0030483 A1     Feb. 8, 2007

(51) Int. Cl.
    *G01J 3/28*     (2006.01)
(52) U.S. Cl. .................................................. 356/328
(58) Field of Classification Search ................ 356/328, 356/479
    See application file for complete search history.

(56) References Cited

U.S. PATENT DOCUMENTS

| | | | | |
|---|---|---|---|---|
| 5,565,986 A | | 10/1996 | Knüttel | 356/346 |
| 5,757,483 A | * | 5/1998 | Pierce, III | 356/328 |
| 6,362,879 B1 | * | 3/2002 | Ranalli | 356/328 |
| 6,487,019 B2 | | 11/2002 | Hoose | 359/575 |
| 6,570,652 B1 | * | 5/2003 | Cappiello | 356/328 |
| 6,577,786 B1 | | 6/2003 | Cappiello et al. | 385/24 |
| 6,628,383 B1 | | 9/2003 | Hilliard | 356/305 |
| 6,657,727 B1 | | 12/2003 | Izatt et al. | 356/450 |
| 6,710,330 B1 | | 3/2004 | Tagami et al. | 250/234 |
| 6,724,533 B2 | | 4/2004 | Hoose et al. | 359/572 |
| 6,754,006 B2 | | 6/2004 | Barton et al. | 359/569 |
| 6,757,113 B1 | | 6/2004 | Basavanhally et al. | 359/819 |
| 6,813,019 B2 | | 11/2004 | Hammer et al. | 356/330 |
| 6,847,454 B2 | | 1/2005 | Crowley et al. | 356/479 |
| 6,859,317 B1 | | 2/2005 | Cappiello et al. | 359/569 |
| 7,034,935 B1 | * | 4/2006 | Kruzelecky | 356/328 |

(Continued)

FOREIGN PATENT DOCUMENTS

CA     2 476 174     9/2003

(Continued)

OTHER PUBLICATIONS

J.F. de Boer et al., Improved signal-to-noise ratio in spectral-domain compared with time-domain optical coherence tomography, *Optics Letters*, vol. 28, No. 21, Nov. 1, 2003, pp. 2067-2069.

(Continued)

*Primary Examiner*—Kara E Geisel
(74) *Attorney, Agent, or Firm*—Stallman & Pollock LLP

(57) ABSTRACT

A compact conical diffraction Littrow spectrometer is disclosed. The distortion of the conically diffracted spectral component beams is compensated and as a result, the diffracted spectral beams can still be focused into a substantially straight line to shine onto a detector array. A spectral domain optical coherence tomography (SD-OCT) system incorporating a Littrow spectrometer or a spectrometer having one or more shared focusing element(s) and an SD-OCT system incorporating a spectrometer that is substantially polarization independent are also disclosed.

51 Claims, 13 Drawing Sheets

U.S. PATENT DOCUMENTS

| | | | |
|---|---|---|---|
| 2001/0048526 A1* | 12/2001 | Bender | 356/328 |
| 2001/0052980 A1* | 12/2001 | Tada | 356/328 |
| 2002/0054289 A1* | 5/2002 | Thibault et al. | 356/328 |
| 2003/0016355 A1 | 1/2003 | Koike et al. | 356/328 |
| 2004/0196458 A1* | 10/2004 | Shimizu et al. | 356/328 |
| 2004/0239938 A1 | 12/2004 | Izatt | 356/450 |
| 2004/0239943 A1 | 12/2004 | Izatt et al. | 356/479 |
| 2005/0018201 A1 | 1/2005 | de Boer et al. | 356/479 |
| 2006/0072424 A1* | 4/2006 | Everett et al. | 369/112.01 |

FOREIGN PATENT DOCUMENTS

| | | |
|---|---|---|
| GB | 1168325 | 10/1969 |
| JP | 2000-46729 | 2/2000 |
| JP | 2001-174404 | 6/2001 |
| WO | WO 03/062802 A2 | 7/2003 |
| WO | WO 2004/043245 A1 | 5/2004 |

OTHER PUBLICATIONS

M.A. Choma et al., "Sensitivity advantage of swept source and Fourier domain optical coherence tomography," *Optics Express*, vol. 11, No. 18, Sep. 8, 2003, pp. 2183-2189.

R.A. Leitgeb et al., "Phase-shifting algorithm to achieve high-speed long-depth-range probing by frequency-domain optical coherence tomography," *Optics Letters*, vol. 28, No. 22, Nov. 15, 2003.

R. Leitgeb et al., "Performance of fourier domain vs. time domain optical coherence tomography," *Optics Express*, vol. 11, No. 8, Apr. 21, 2003, pp. 889-894.

D. Maystre et al., "Geometrical invariance property of gratings," *Applied Optics*, vol. 24, No. 2, Jan. 15, 1985, pp. 215-216.

T. Matsui, "Dynamic Range of Optical Reflectometry with Spectral Interferometry," *Jpn. J. Appl. Phys.*, vol. 38, Part 1, No. 10, Oct. 1999, pp. 6133-6137.

E. Popov et al., "Almost perfect blazing by photonic crystal rod gratings," *Applied Optics*, vol. 40, No. 15, May 20, 2001, pp. 2417-2422.

L. M. Smith et al., "Absolute displacement measurements using modulation of the spectrum of white light in a Michelson interferometer," *Applied Optics*, vol. 28, No. 15, Aug. 15, 1989, pp. 3339-3342.

M. Wojtkowski et al., "Real-time in vivo imaging by high-speed spectral optical coherence tomography," *Optics Letters*, vol. 28, No. 19, Oct. 1, 2003, pp. 1745-1747.

I. Zeylikovich et al., "Nonmechanical grating-generated scanning coherence microscopy," *Optics Letters*, vol. 28, No. 23, Dec. 1, 1998, pp. 1797-1799.

Brochure, Laser & ASE Systems, "Rapid Scan Tunable Lasers," *Thorlab Inc. Product Catalog*, vol. 17 (2005), 1 page in length.

* cited by examiner

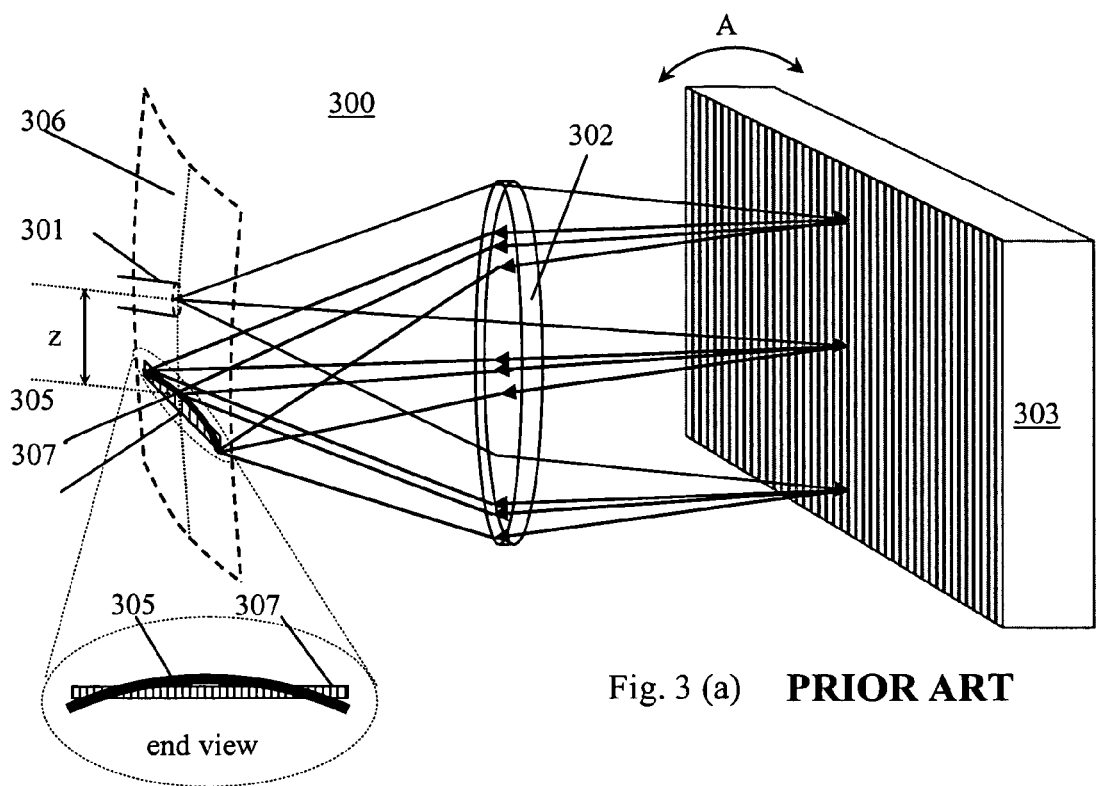
Fig. 3 (a) PRIOR ART
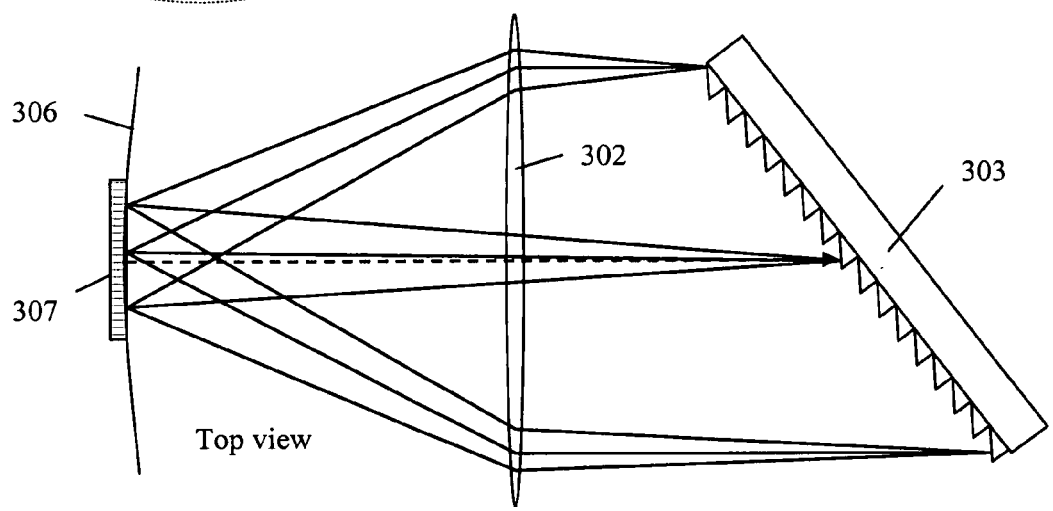
Fig. 3 (b) PRIOR ART

Top view

LITTROW SPECTROMETER AND A SPECTRAL DOMAIN OPTICAL COHERENCE TOMOGRAPHY SYSTEM WITH A LITTROW SPECTROMETER

BACKGROUND OF THE INVENTION

1. Field of the Invention

The invention relates generally to optical spectrometers and to the use of a Littrow configuration spectrometer in a spectral domain optical coherence tomography system.

2. Description of Related Art

Optical Coherence Tomography (OCT) is a technology for performing high-resolution cross sectional imaging that can provide images of tissue structure on the micron scale in situ and in real time. In recent years, it has been demonstrated that spectral domain OCT has significant advantages in speed as compared to time domain OCT. In spectral domain OCT, the optical path length difference between the sample and reference arm is not mechanically scanned but rather the interferometrically combined beam is sent to a spectrometer in which different wavelength components are dispersed onto different photodetectors to form a spatially oscillating interference fringe (Smith, L. M. and C. C. Dobson (1989). "Absolute displacement measurements using modulation of the spectrum of white light in a Michelson interferometer." *Applied Optics* 28(15): 3339-3342). A Fourier transform of the spatially oscillating intensity distribution can provide the information of the reflectance distribution along the depth within the sample. As there is no mechanical depth scanning, acquisition of light reflection along a full depth range within the sample can be achieved simultaneously, and consequently, the speed of obtaining a full depth reflection image is substantially increased as compared to time domain OCT (Wojtkowski, M., et al. (2003). "Real-time in vivo imaging by high-speed spectral optical coherence tomography." *Optics Letters* 28(19): 1745-1747; Leitgeb, R. A., et al. (2003). "Phase-shifting algorithm to achieve high-speed long-depth-range probing by frequency-domain optical coherence tomography." *Optics Letters* 28(22): 2201-2203). In addition, as the light reflected from the full depth range within the sample is fully dispersed over many photodetectors, the shot noise for each photodetector is substantially reduced as compared to the time domain OCT case, and hence the signal to noise ratio can also be substantially increased (Leitgeb, R. A., et al. (2003). "Performance of Fourier domain vs. time domain optical coherence tomography." *Optics Express* 11(8): 889-894; De-Boer, J. F., et al. (2003). "Improved signal-to-noise ratio in spectral-domain compared with time-domain optical coherence tomography." *Optics Letters* 28(21): 2067-2069; Choma, M. A., M. V. Sarunic, et al. (2003). "Sensitivity advantage of swept source and Fourier domain optical coherence tomography." *Optics Express* 11(18): 2183-2189)

In most high speed spectral domain optical coherence tomography (SD-OCT) designs, a spectrometer is used with a diffraction grating that disperses the incident beam into its spectral components and a detector array that receives the dispersed spectral components. Typically, an SD-OCT system uses the classical or in-plane diffraction configuration with the incident and diffracted beams all perpendicular to the grating grooves (see for example: JP2000-046729, U.S. Pat. No. 5,565,986, JP2000-046729, JP2001-174404, WO03062802 (US20050018201), U.S. Pat. No. 2,476,174, WO2004043245, US20040239938 (WO2004111929)). In such a case, the dispersed spectral component beams are co-planar with the incident beam and can thus be relatively easily focused into a line to shine onto a detector array for detection of the interference spectrum. However, due to the large extent of the dispersed spectrum in the plane of the incident and dispersed beams, the incident and diffracted beams generally do not share a common lens, as doing so would put the incident beam at a large off-axis angle, which tends to cause distortion in the incident beam and this distortion carries through to the diffracted beams. In order to reduce the off-axis distortion of both the diffracted beams and the incident beam, two separate lenses are generally used and a relatively large angle between incidence and diffraction is required. A problem associated with such a design is that the size of the spectrometer will be large and in addition, when a standard high speed (>1000 lines/sec) line scan camera is used as the detector array, owing to the small height of the linear array pixels (about 10 microns), the spectrometer output can be very sensitive to the tip movement of the focused spectral line with respect to the linear array pixels caused by mechanical vibration and temperature variation.

In order to reduce the size of the spectrometer, a Littrow configuration can be used. The term Littrow configuration is sometimes used to describe an arrangement where the diffracted light of interest propagates back along the propagation axis of the incoming beam. Those skilled in the art often use the term Littrow configuration more broadly to define an arrangement wherein some of the diffracted light beams of interest propagate close to the propagation axis of the incoming beam. The specification and claims will use the term Littrow configuration (or arrangement or condition) as it is more broadly defined. As an alterative to using this term, a compact spectrometer arrangement can also be defined as a configuration where a common lens is used to focus both the incoming and diffracted beams of interest.

In a basic Littrow configuration, the small separation between the incoming and diffracted beams of interest can result in some spatial overlap, making detection schemes more difficult to implement. This difficulty can be overcome by tilting or tipping the grating so that the incident wave vector of the incoming beam strikes the grooves of the grating at a non-normal angle. In this configuration, conical diffraction is created which results in the diffracted beam being separated from the propagation axis of the incoming beam. This separation is along an axis perpendicular to the plane defined by the incoming and diffracted beams and, for simplicity, will sometimes be referred to herein as a vertical separation of the beams. Even though the tipping of the grating results in the vertical separation of the diffracted beam from the incoming beam, those skilled in the art still generally refer to this arrangement as a Littrow configuration. The specification and claims will use the phrase "substantially Littrow" to cover all variants of the Littrow configuration (both in-plane and conical) and to distinguish the configuration from the prior art spectrometers which had large angles between the incoming beam and the diffracted beams being measured.

Littrow spectrometers have been used in the prior art. Most are of the classical in-plane diffraction design (see, U.S. Pat. No. 6,757,113). Littrow spectrometers have also been suggested that use conical diffraction to create vertical separation between the incoming and diffracted beams to be detected (see, U.S. Pat. No. 6,710,330). These designs still permit both the incoming and diffracted beams to be measured to share a common lens. As a result, the spectrometer can be compact with a substantially reduced size. This Littrow configuration also allows the spectrometer to be made highly stable to withstand mechanical vibration and temperature variation.

On problem with the prior art Littrow spectrometers which utilize conical diffraction is that the conical diffraction creates certain distortions and non-linearities in the focused beam. These problems are described in greater detail below with respect to FIG. 3. One aspect of the subject invention is to provide optical correction for such distortions.

It should also be noted that although a grating in a Littrow configuration has been reported in some OCT systems, these systems are not spectral domain OCT systems. Instead, the in-plane Littrow diffraction is employed to generate a reference beam with laterally displaced multiple optical path lengths and it did not use conical diffraction. See, for example: U.S. Pat. No. 6,847,454, and Zeylikovich, I. et al. (1998), "Nonmechanical grating-generated scanning coherence microscopy," Optics Letters 23(23): 1797-1799), both of which differ from the present invention wherein a Littrow spectrometer is used in an SD-OCT system to disperse the interfered beam in the detection arm into its spectral components and to focus the dispersed spectral components onto a detector array.

SUMMARY OF THE INVENTION

The present invention discloses an improved design for Littrow spectrometers and the use of such spectrometers for SD-OCT systems.

The spectrometer includes a grating for dispersing the incoming light beam as a function of wavelength. A linear detector array receives and measures the diffracted, dispersed light of interest. The incoming beam, grating and the array are preferably positioned in a substantially Littrow condition so that the diffracted beam propagates along an axis near to the incoming beam. In an alternative definitional approach, the incoming and diffracted beam to be measured share a common optical focusing element. Both of these descriptions define a compact spectrometer.

The orientation of the grating is tilted or tipped to induce conical diffraction in order to spatially separate the incoming beam from the diffracted beams to be measured. The conical diffraction will create certain non-linearities in the footprint of the beam with respect to the planar linear array. In one aspect of the invention, optical elements are provided for reducing these non-linearities.

In another aspect of the invention, the compact spectrometer is used as the detecting element in a spectral domain optical coherence tomography system (SD-OCT). In one embodiment, the spectrometer is in a substantially Littrow configuration. Alternatively, the spectrometer includes a common lens for focusing both the incoming and diffracted beams that are measured. In either case, it is preferable, though not necessary to use conical diffraction to vertically separate the incoming and diffracted beams. In the case of conical diffraction, it is preferable, but not required, to provide for correction for distortion and/or non-linearities in the footprint of the diffracted beam.

Various other possible improvements are possible for a preferred spectrometer. For example, the spectrometer can be designed with features to reduce the sensitivity to thermal variations. In addition, the spectrometer can be designed to generate an output that is substantially insensitive to the polarization state of the incoming beam.

These and other features and advantages of the present invention will become more readily apparent to those skilled in the art upon review of the following detailed description of the preferred embodiments taken in conjunction with the accompanying drawings.

BRIEF DESCRIPTION OF THE DRAWINGS

FIG. 3($a$) shows a perspective view of Littrow conical diffraction, in which the light is diffracted back approximately toward the direction of incidence, and the incident and diffracted light beams are also separated from each other through conical diffraction.

FIG. 3($b$) shows a top view of the configuration of FIG. 3($a$)

FIG. 10($b$) shows that with the insertion and appropriate placement of a field flattening lens that has an approximately 3.1% positive (pincushion) distortion, the focused spectral line can be straightened to have only a maximum of 1 micron deviation from a straight line.

FIG. 12(d) shows a grating with a substrate and a reflective material adjacent the substrate to render the grating substantially polarization independent FIG. 12(e) shows a blazed photonic crystal grating made with embedded circular rods in another optical medium that has a high diffraction efficiency and a high degree of polarization independence

DETAILED DESCRIPTION OF THE INVENTION

As is well known to those skilled in the art, a broad band light beam can be dispersed into its spectral components in a number of ways, including the use of a prism, a grating, an arrayed waveguide grating or a combination of optical filters. A grating is generally used in most spectrometers because of its high resolving power and hence high spectral resolution within a limited space. In many applications, a plane grating is preferred because of its low cost as compared to other more complex gratings such as a curved grating, a volume holographic grating, or a photonic crystal grating.

Figure 1:
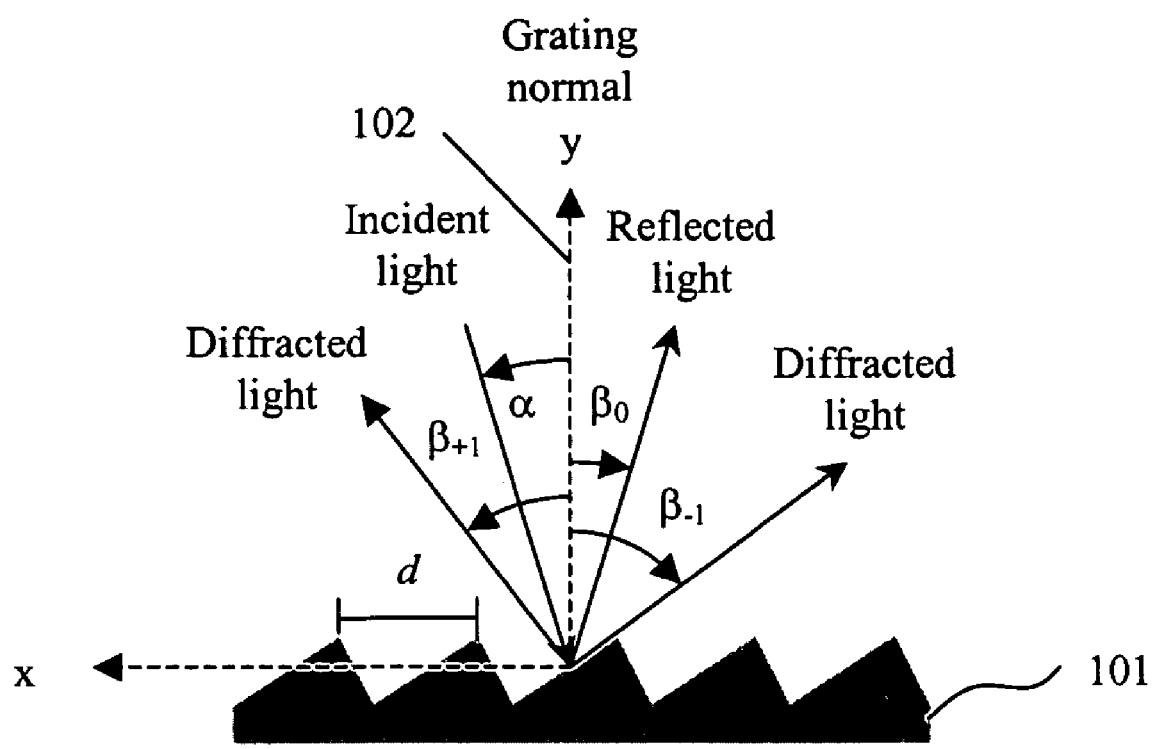
FIG. 1 shows a plane reflection grating being used in the normal classical or in-plane configuration to diffract an incident light beam into multiple diffracted orders.

FIG. 1 shows the case of a plane reflection grating 101, the grating equation is given by $$m\lambda = d(\sin\alpha + \sin\beta_m) \quad (1)$$

where m is the diffraction order which is an integer, $\lambda$ is the wavelength of light, d is the grating period, $\alpha$ is the angle of incidence, and $\beta_m$ is the angle of diffraction. The angle of incidence and angle of diffraction are measured from the grating normal 102, i.e. the dashed line perpendicular to the grating surface. The angle sign convention is that angles measured counter-clockwise from the normal are positive and angles measured clockwise from the normal are negative. We denote the x-axis in FIG. 1, the axis in the plane of the grating perpendicular to the grooves, as the dispersion axis.

For a given diffraction order m, the angular dependence of the diffracted spectral components upon the wavelength is given by $$\beta_m(\lambda) = \arcsin\{m\lambda - \sin\alpha\} \quad (2)$$

It should be pointed out that the validity of Equ. (1) is restricted to cases in which the incident and diffracted light rays are perpendicular to the grating grooves, which is called the classical or in-plane diffraction.

Figure 2:
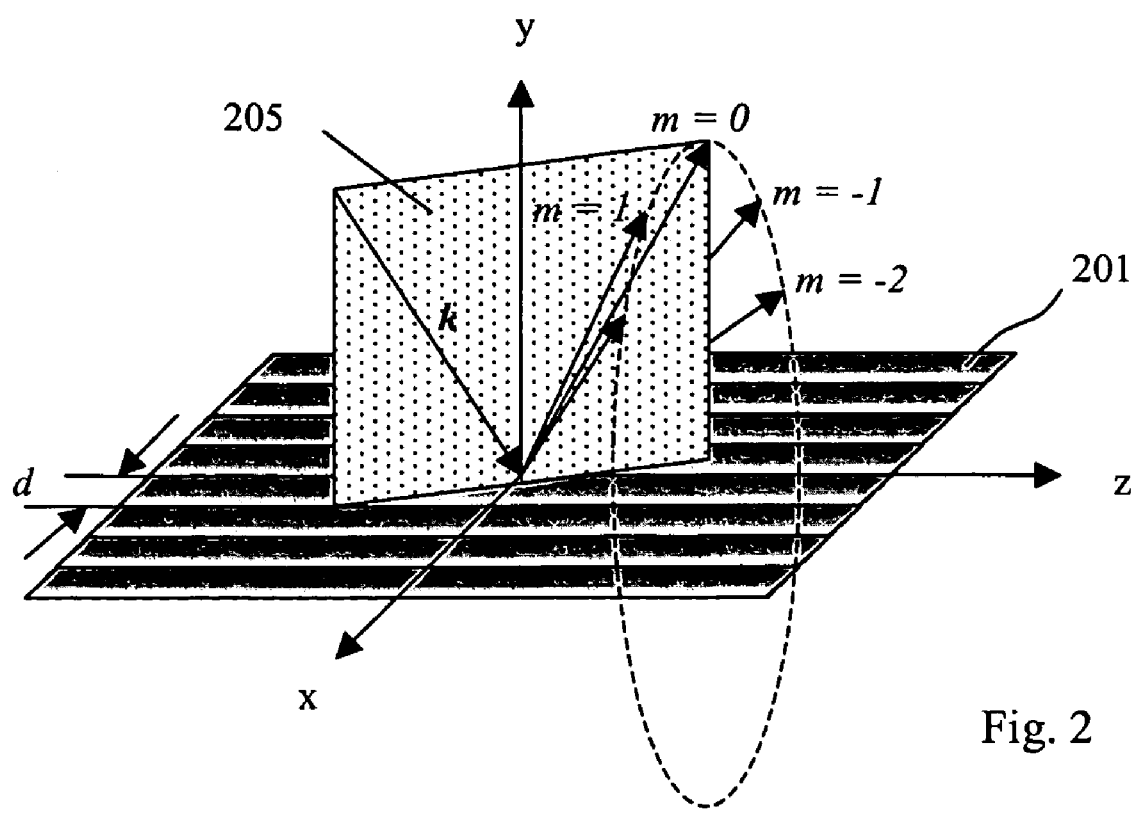
FIG. 2 shows a general case of conical diffraction where a rectangular coordinate system Oxyz is assumed with the grating groove parallel to the z-axis.

If the incident light beam is not perpendicular to the grooves, the grating equation must be modified to $$m\lambda = d\cos\epsilon(\sin\alpha + \sin\beta_m) \quad (3)$$

where $\epsilon$ is the angle between the incident light path and the plane perpendicular to the grooves. When $\epsilon \neq 0$, the diffracted spectra lie on a cone rather than a plane and the diffraction is called conical diffraction. To better understand conical diffraction, let us consider a rectangular coordinate system Oxyz with the grating groove 201 parallel to the z-axis as shown in FIG. 2. An incident plane wave, with a wave vector of $k=(k_x e_x + k_y e_y + k_z e_z)$ and its modulus $|k|=(2\pi/\lambda)$, falls on the grating at an arbitrary off-plane direction as shown by the dotted plane 205 in FIG. 2. From diffraction theory (see for example, Maystre D. et al. (1985) "Geometrical invariance property of gratings" Applied Optics 24(2): 215-216), $$k_{mx} = k_x + m\frac{2\pi}{d} \quad (4)$$

$$k_{my} = \sqrt{k^2 - k_{mx}^2 - k_{mz}^2}$$

$$k_{mz} = k_z$$

The above equation tells us that $k_m$ and k have the same modulus. As $k_{mz}=k_z$ for all the diffraction orders m, the various diffracted order wave vectors will lie on a cone formed by the origin of the coordinate system Oxyz and the dashed circle as shown in FIG. 2. The projection of all the diffracted order wave vectors onto the xy plane will result in a diagram similar to FIG. 1 with the difference that the xy plane component modulus of the various diffracted order wave vectors is the projection of k onto the xy plane, i.e. $|k_{mx}e_x + k_{my}e_y| = |k_x e_x + k_y e_y| = |k|\cos\epsilon$, where $\epsilon$ is the angle between the incident wave vector and the xy plane. Therefore, Equ. (3) instead of Equ. (1) should be used and the angles in Equ. (3) are those corresponding to the wave vectors projected onto the xy plane.

The efficiency of diffraction for a particular diffraction order m can be adjusted by changing the groove facet angles, or their shape and depth. The optimization of efficiency by appropriate groove shaping is known as blazing. In many applications, planar blazed holographic gratings and planar blazed diffraction gratings are used because of their high efficiency combined with their low cost and high resolving power.

A particularly useful case is a blazed diffraction grating operating in the Littrow configuration where the grating is set at an angle such that, for the range of wavelengths collected and the desired order of diffraction m, approximately $\alpha \approx \beta_m$; the diffracted beams nearly return on the path of the incident beam. (see for example, U.S. Pat. No. 6,710,330, U.S. Pat. No. 6,859,317).

FIG. 3(a) shows a perspective view of an example of a conical diffraction Littrow configuration 300, in which light from an optical fiber 301 is collimated by a common lens 302 and propagates towards a blazed reflection grating 303. To create conical diffraction, the grating is tilted or tipped about the axis shown by arrow A. If the grating were not tipped, and oriented such that the incident light was perpendicular to the grating grooves, the diffracted light would return along the path of the incident beam so that the footprint 305 of the diffracted light would form a spectrum substantially centered on the output end of the fiber 301 (i.e. the in-plane Littrow condition). (See also the top view of FIG. 3(b).)

Tipping the grating creates conical diffraction which, as shown in FIG. 3(a), vertically displaces the footprint of the diffracted light by an amount "z" thereby permitting the light to be detected by pixel array 307.

A key issue with such an arrangement, however, is that due to the non-planar effects introduced by conical diffraction, the diffracted light beam vectors will lie on the surface of a cone and as a result, when the spectrally dispersed beams are focused by lens 302, the footprint of the focused light will be curved 305 (as can be seen from the inset end view in FIG. 3(a)). More particularly, the footprint will have a non-linearity with respect to the linear axis of the detector array such that the focused region will be higher on the z axis at the center of the array than at the opposed ends. If a standard linear detector array 307 such as that of a line scan camera is used, depending on the spectral width of the input beam, portions of the focused curved spectral line may fall outside the photosensitive area of the detector array 307. This is especially true for a high axial resolution SD-OCT system in which a broadband light source is desired. In addition, such a focused curved spectral line may also make the spectrometer output very sensitive to mechanical vibration and temperature changes that may cause portions of the focused spectral line fall off the pixels.

One possible solution is to use a curved rather than a standard linear detector array to match the shape of the curved focused spectral line. However, this would require a custommade line scan camera and hence would mean a high cost. A second solution is to make the shape of the detector array pixels rectangular rather than square as is commonly the case for line scan cameras so that they can tolerate some movement of the focused spectral line with respect to the pixels. The larger photosensitive area of such taller rectangular pixels, however, implies greater capacitance of the photosensitive area, which makes fast readout more difficult. While such an aspect is one of the preferred embodiments of the present invention, most commercial high-speed line scan cameras are meant for completely different applications such as for optical document scanners, and hence the pixel height of these cameras is generally not large enough to compensate for the bending of the focused spectral line resulting from the broad bandwidth of a light source for a high axial resolution SD-OCT system.

As a first key feature of the present invention, a lens is selected for reducing the non-linearity caused by the conical diffraction so that the registration of the footprint of the diffracted beam and the array is improved.

Figure 4:
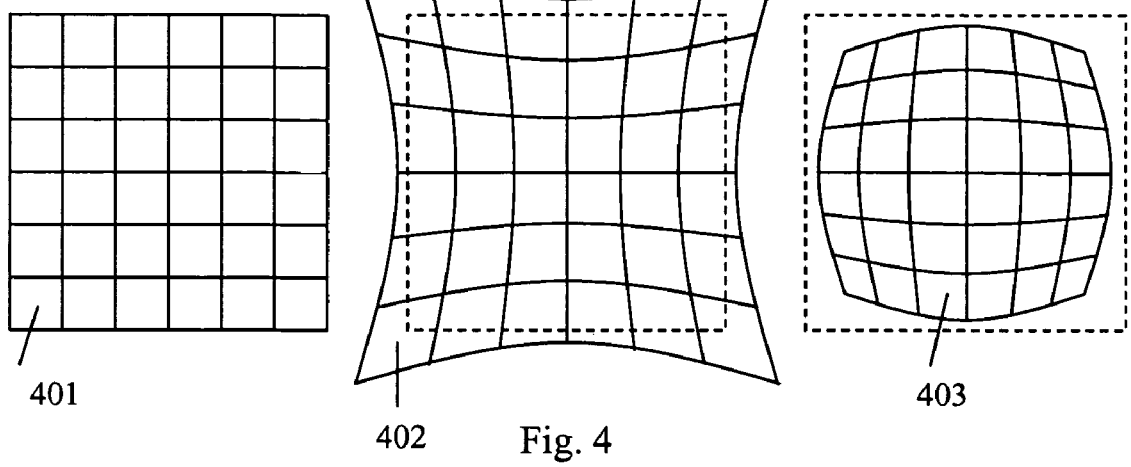
FIG. 4 shows distortion due to lens aberration, in which the left image is a perfect image without any distortion, the middle one is an image with positive (also called pincushion) distortion and the right one is an image with negative (also called barrel) distortion.

As is well known to those skilled in the art, an aberrant lens can have a positive (also called pincushion) distortion or a negative (also called barrel) distortion as shown in FIG. 4, in which the left image 401 is a perfect image without any distortion, the middle one 402 is an image with positive distortion and the right one 403 is an image with negative distortion.

Figure 5:
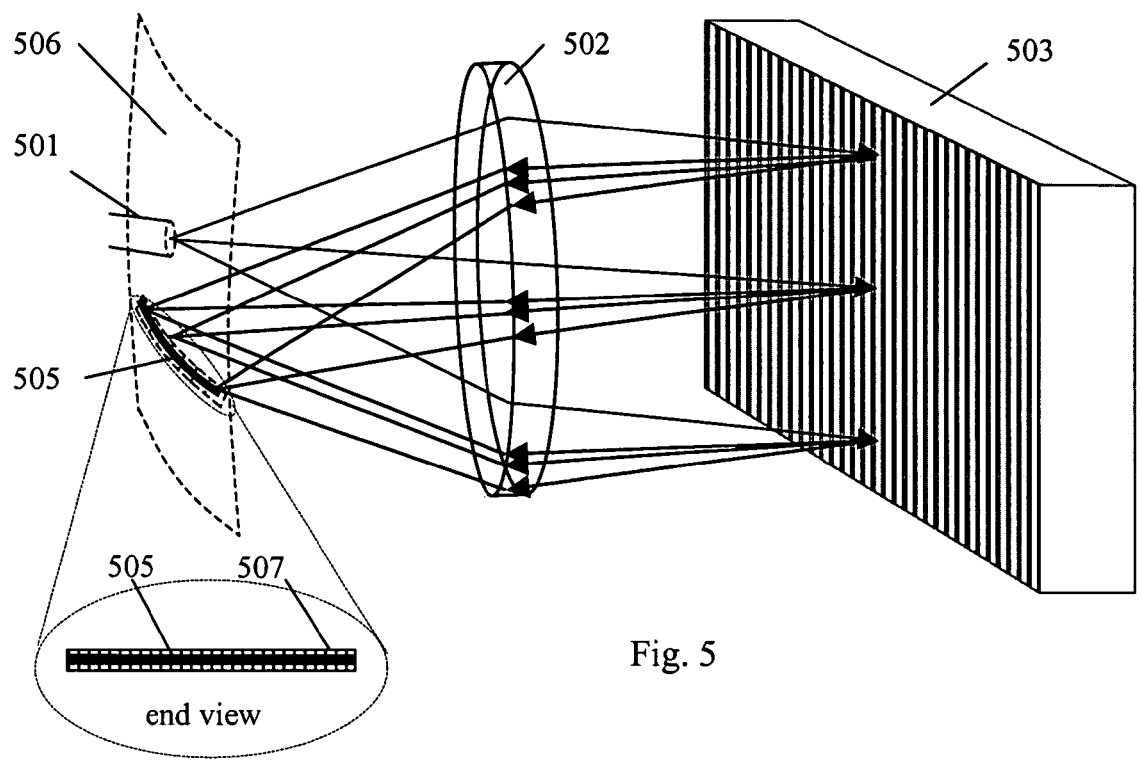
FIG. 5 shows a preferred embodiment of a Littrow conical diffraction configuration in which a lens with a negative distortion is placed in the optical path with a certain vertical off axis displacement so that the conically diffracted beams will suffer a negative distortion from the aberrant lens that substantially compensates the positive distortion of the diffracted beam FIG. 6($a$) shows perspective view of a preferred embodiment of the presently invented conical diffraction based Littrow spectrometer in which a field flattening lens is used to further straighten the focused spectral line, an input port lens is used for numerical aperture matching and a deflecting mirror is arranged in the front of the detector array to further reduced the overall size of the spectrometer.

FIG. 5 illustrates a preferred approach for compensating for the bending of the focused spectral line 305 caused by conical diffraction as shown in FIG. 3(*a*). More specifically, a common (generally thicker) aberrant lens 502 with a negative (barrel) distortion is preferably placed in the optical path of both the input and the output arms with a certain vertical off axis displacement for the output beams as shown in FIG. 5. The principal central ray of the input beam from the optical fiber 501 will pass the common lens 502 through the vertical central line of the lens and the principal central light rays of the conically diffracted beams from the grating 503 will pass through the common lens 502 from the lower half of the lens, thus suffering a negative distortion from the lens that substantially compensates the positive distortion of the conically diffracted beams. As a result, the imaged spectrally dispersed line 505 on the curved image surface 506 is substantially straightened laterally as can be seen from the inset end view of FIG. 5.

Note that the above paragraph should not be interpreted as limiting the invention to the use of the common lens in a Littrow spectrometer for compensating the distortion of conically diffracted light beams. The distortion of conically diffracted beams in a Littrow spectrometer can also be compensated in other ways. For example, the lens used for distortion compensation can be a separate lens only for the output arm of the spectrometer. However, a more compact arrangement can be achieved by sharing the lens in front of the grating. In addition, the spectrally dispersed beams do not need to be limited to the same diffraction order and can include overlapping diffraction orders, possibly with some crossed dispersion to separate the orders vertically. Furthermore, the present invention is not limited to the use of off-axis-image-induced-distortion compensation; other types of lenses can also be used as long as they can achieve a similar effect. For example, a lens with a positive distortion can also be used as long as the spectrally diffracted beams are arranged such that the principal central rays will pass the lens through the upper half of the lens, assuming that the grating is tipped toward the lens, or the lower half if the grating is tipped away. Alternatively, a specially designed lens can also be used in such a way that even if the principal central rays of the diffracted beams will pass the vertical central part of the lens, the lens will still introduce a compensating distortion to straighten the focused spectral line.

An issue that may be associated with the spectrometer as shown in FIG. 5 is that the well focused spectral line may still lie on a curved surface 506 (also seen as 306 in FIG. 3(*b*)) of positive curvature as is often the case for a conventional imaging system. The result of this curved surface 506 of good focus is that the spectral line cannot be well focused onto all the pixels of a planar detector array. Instead, the focused spot size on each pixel will vary across the sensor.

Figure 6A:
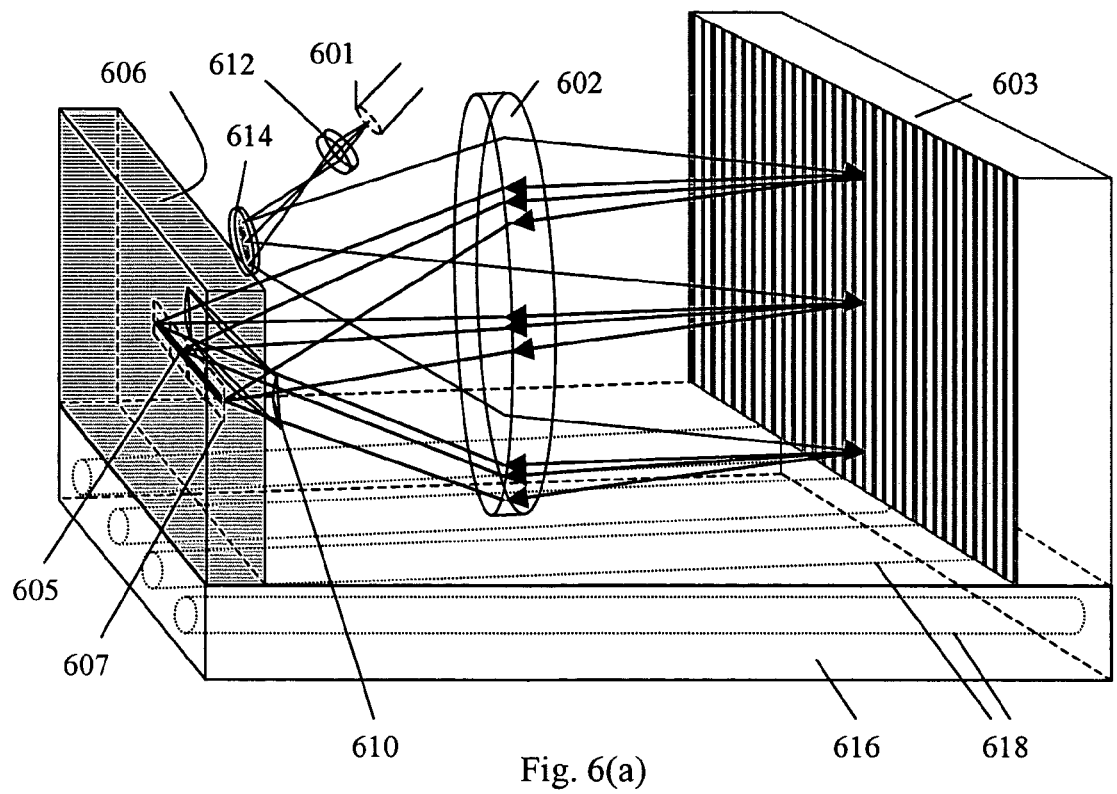
FIG. 6($b$) shows a top view of FIG. 6($a$)
Figure 6B:
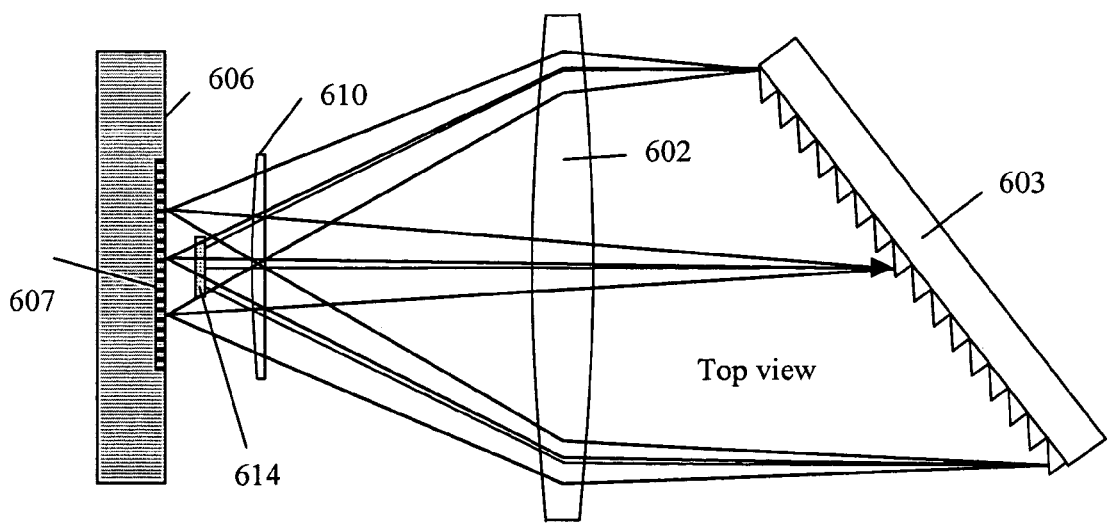

As a solution to this problems, according to one or more embodiments of the present invention, a field flattening lens 610 is inserted in the output arm in front of the linear detector array 607 to substantially flatten the surface of good focus so that the focal points of the spectral line 605 can be well aligned on the flat surface 606 of the detector array as shown in FIGS. 6(*a*) and (*b*). It should be understood that the above-mentioned field flattening lens can be in any suitable form such as in the form of a meniscus lens. The field flattening effect can also be achieved through the design of the common lens, or the use of a combination of lenses. Thus, in a preferred embodiment, the invention provides an approach to substantially straighten the focused spectral line in a conical diffraction Littrow spectrometer wherein compensation is provided for either or both the distortion of the spectrally dispersed beam in the transverse direction (across the array as seen in FIG. 5) or in the direction of propagation of the beam (corrected by field flattening lens of FIG. 6). Such distortion compensation should be interpreted as a way to straighten the focused spectral line in a 3D space so that a planar photodetector array can be aligned with the straightened focused spectral line to enable a stable and true conversion of the optical energy as a function of wavelength into electrical signals.

Another issue that may be associated with the configuration of FIG. 5 is that when the input beam comes from a single mode optical fiber as is the case for most practical-SD-OCT systems, the numerical aperture of the fiber may not match the numerical aperture of the spectrometer. As one additional feature of the present invention, an input lens 612 is inserted in the input arm near the fiber tip 601 to match the numerical aperture of the input arm to that of the output arm as is also shown in FIG. 6(*a*). It should be understood that there are other ways to change the numerical aperture of the light coming out of a single mode fiber tip, for example, the numerical aperture can be changed by shaping the fiber tip into a lens directly or attaching a grin lens to the fiber Still another issue of the configuration as shown in FIG. 5 is that the packaged size of commercially available line scan cameras are generally much larger than the photosensitive area of the pixel array. Hence it is not possible to put an optical fiber just above the pixel array from behind the camera body. As one preferred additional feature of the present invention, a light beam folding mirror 614 is mounted in the front of the line scan camera as shown in FIGS. 6(*a*) and (*b*) so that the relative angle between the input arm and the output arm can be kept small, for example, less than about 10 degrees. This arrangement can scale down the degree of distortion introduced to the diffracted spectral line by conical diffraction since the diffraction now approaches the classical in-plane diffraction. The arrangement also substantially reduces the size of the whole spectrometer to make it more compact and also more stable.

In application to SD-OCT, relatively large static misalignments that move the spectrum along the line-scan pixel array can be tolerated. Such lateral misalignments shift the recorded spectral interference fringes, but do not change their spatial frequency, to first order in the shift. The frequency of the fringes changes only through the non-linearity in the relation between optical frequency and position on the line-scan pixel array. The relation between the position, parameterized by a variable x running from −0.5 to +0.5 along the pixel array, and optical frequency ν can be approximated by a polynomial. As an example, for a Littrow configuration covering a range Δν of optical frequencies that is 10% of the central optical frequency, a typical approximate relation is $\nu=C[x+0.15x^2+0.05x^3]$ where C is a constant. Those skilled in the art of OCT can compute the impact on OCT image quality of an un-compensated shift δx of the spectrum relative to the camera. A shift of δx=0.05, ten pixels on a 2048-pixel camera, is often tolerable.

Due to the limited height of the pixels in most commercially available high-speed line scan cameras and the diffraction limited focused spot size of the spectral line, the spectrometer output is most sensitive to vertical misalignments because misalignment of one pixel causes the light to miss the photosensitive area.

Figure 7:
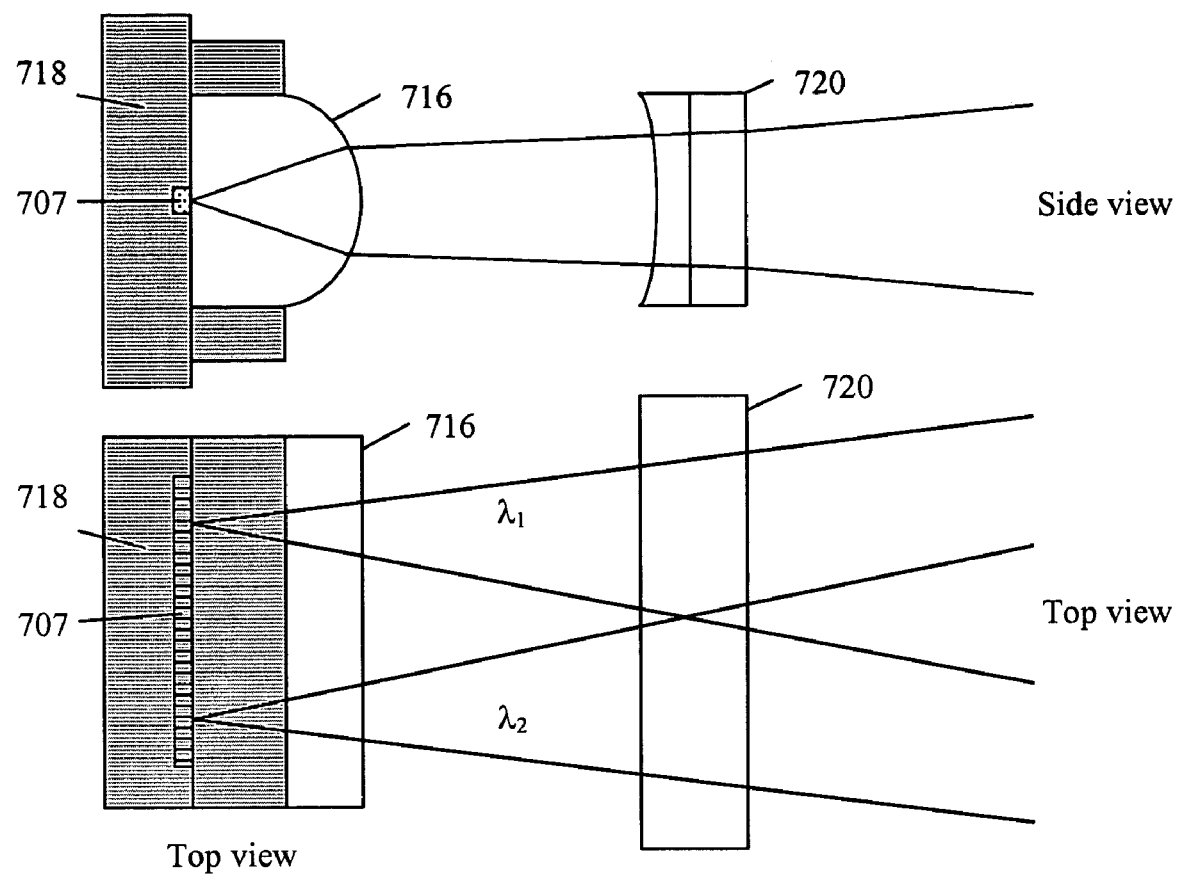
FIG. 7 shows a cylindrical lens closely and rigidly mounted to the detector array that reduces the sensitivity of vertical misalignment caused by mechanical and/or temperature drift.

In one preferred embodiment of the invention, a cylindrical lens 716 closely and substantially rigidly mounted to the line-scan camera 718 as shown in FIG. 7 significantly reduces the sensitivity of vertical misalignment caused by mechanical and/or temperature drift. FIG. 7 shows two orthogonal views of the line-scan detector array 707, closely mounted cylindrical lens 716, and a compensating cylindrical lens 720 to be discussed later. The upper section of FIG. 7 shows the view along the length of the line-scan detector array 707. The short focal-length cylindrical lens 716 focuses the diffracted spectral beams onto the pixel array 707. If the diffracted spectral beams are initially vertically collimated, all light rays at the same vertical angle are focused at the same point vertically, so mechanical drift causing displacement of the pixel array 707 and this cylindrical lens 716 together will cause no loss of light to the line scan camera, until the displacement is comparable to the size of the cylindrical lens 716.

The arrangement of FIG. 7 can be used by itself to improve the operation of a line-scan camera. In a preferred embodiment, the arrangement of FIG. 7 is used in combination with the configurations shown in either FIG. 5 or 6. In this regard, it should be noted that the diffracted light beams propagating towards the cylindrical lens 716 do not need to be initially vertically collimated and the shared lens 602 or the field flattening lens 610 as discussed in FIG. 6 can have an astigmatism that provides the required correction for the cylindrical lens 716.

A range of vertical angles of incoming light will be focused by the cylindrical lens 716 onto the finite-sized pixel. If, for example, the focal length of the cylindrical lens 716 is approximately 5 mm, and the height of the pixels is 10 microns, then the acceptance angle is approximately 2 milliradians. This vertical angular tolerance is improved from the angular tolerance of the diffracted beam angles (determined by the grating tilt) compared to when we illuminate the linear pixel array without this cylindrical lens. In direct illumination, the angular tolerance is the pixel height divided by the focal length of the shared lens. For example with a 10-micron pixel height and a 200-mm focal length in the spectrometer, the angular tolerance would be 0.05 milliradians.

In order to have individual optical frequencies (wavelengths) brought to focus in both the vertical and lateral directions, the astigmatism introduced by this cylindrical lens 716 can be compensated. A diverging cylindrical lens 720 some distance from the converging lens can compensate, as shown in FIG. 7. This diverging cylindrical lens 720 can advantageously be combined with the field-flattening lens 610 described earlier, by adding the required cylindrical power to that of the field flattening lens 610.

The pair of lenses described above produces an image of the pixels that is magnified vertically, and imaged 1:1 laterally. The benefits of these lenses can be achieved with any anamorphic imaging system that creates an image of the pixel array that is magnified in the vertical direction relative to the lateral direction. The effect of such an anamorphic imaging system is to make a commonly-available line-scan sensor appear optically as though it has tall pixels, without the disadvantage of larger physical photosensitive elements. Sensitivity to mechanical drift between the camera and grating can be reduced by mounting the anamorphic lens set so that it moves substantially with the camera; then each micron drift between camera and grating moves the magnified image by approximately one micron. One implementation of the anamorphic imaging system is to add cylindrical power to each of the field flattening 610 lens and the shared lens 602 shown in FIG. 6. The cylindrical powers can be chosen such that each of the lateral focus and vertical focus of the spectrum lies substantially in the plane of the line-scan detector array, but the rays converge on the pixel array through a broader vertical numerical aperture than lateral numerical aperture. The spot formed on the pixels for each optical frequency or wavelength then has smaller vertical than horizontal extent; if the vertical extent is small compared with the pixel height, some misalignment is tolerated before light is lost from the pixel.

It should be understood that there are many variations to the above design that can produce the same end result. For example, the shared lens 602 can also have a certain astigmatism that compensates the astigmatism of the cylindrical lens 716 in such a way that vertical and lateral focusing of the dispersed spectral beams will overlap on the surface of the pixel array 707, so that the need for the compensating cylindrical lens 720 can be removed. Astigmatism in the shared lens 602 may be canceled by a compensating astigmatism in the input lens 612, or the astigmatism in the shared lens 602 may be tolerated by the grating design. In addition, the function of the field flattening lens 610 can also be combined into the cylindrical lens 716 that is mechanically mounted and substantially rigidly fixed to the line-scan camera 718, so that mechanical drift of the system tends to move the line scan pixels 707 and the combined cylindrical and field flattening lens together. The insensitivity to translation of the line scan camera, explained above in terms of the short focal length rigidly mounted cylindrical lens 716, is thus achieved using only the shared lens 602 with a certain astigmatism and a combined cylindrical and field flattening lens.

As is known to those skilled in the art, lenslet arrays are commonly rigidly mounted to small-pixel detector arrays (such as CMOS detector arrays), often providing the advantage of a light-collecting image of the pixel that is larger than the physical size of the pixel. If such a lenslet array is mounted to a line scan sensor, the lenslet array can be designed to produce magnified images of the individual pixels. The array of magnified pixel images can be used in the present invention in a way similar to the use of the magnified image produced by the anamorphic imaging system of FIG. 7. Two disadvantages of the lenslet array are the tight alignment tolerance required and greater cost relative to the 2-lens system of FIG. 7.

Figure 8:
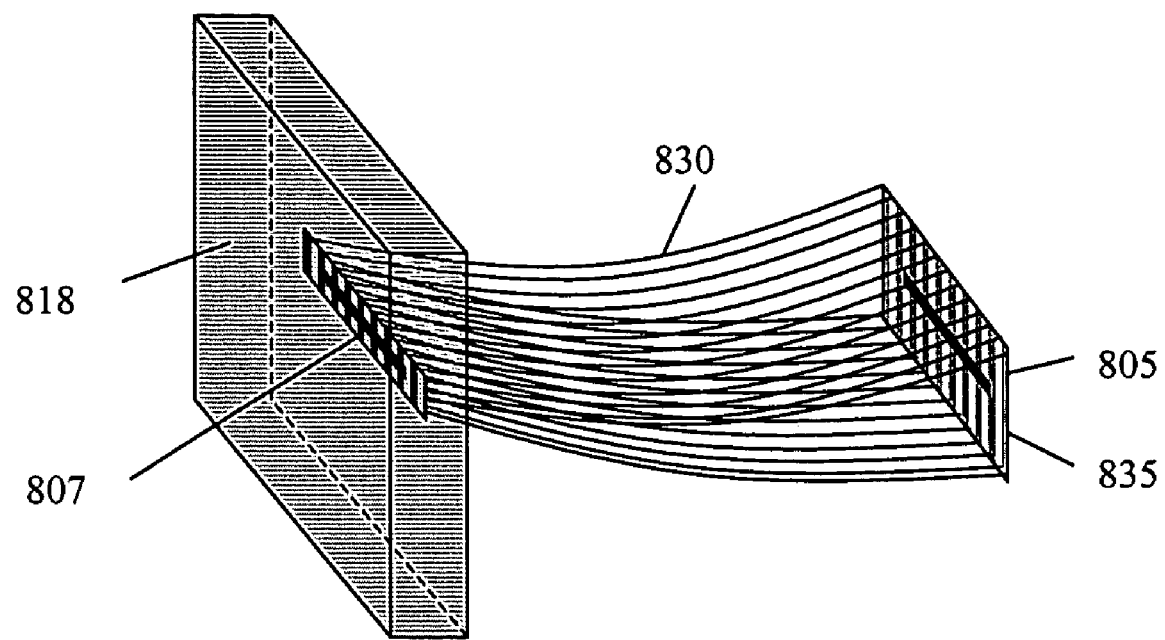
FIG. 8 shows an alternative approach for stabilizing the spectrometer output by using a one dimensional de-magnifying light pipe array to guide the focused spectral line to a detector array.

An alternative approach is to use a vertically de-magnifying light pipe array 830 as shown in FIG. 8, in which case, the de-magnified end of the light pipe array 830 can be aligned with the detector pixel array 807 and rigidly fixed on the line scan camera 818 while the other end of the light pipe array 830 can be mounted to receive the focused spectral line 805. As can be seen in FIG. 8, the large size end of the light pipe array 830 now offers a larger tolerance for the focused spectral line 805 to drift up or down but still within the light capturing surface area 835 to enable the captured light to be channeled to the detector array 807 with minimum loss of light energy. It should be noted that the surface 835 of the large size end of the light pipe array 830 does not need to be restricted to a flat surface. In fact, one can make this surface curved such that its curvature matches that of the focused spectral line when there is no field flattening lens and in this way, the requirement for a field flattening lens can be lessened. Additionally, the light pipe array can also have horizontal magnification as this could also allow use of cameras with different pixel sizes.

In another preferred embodiment of the present invention, the spectrometer is mounted on a base material that has a substantially low thermal expansion. While certain materials such as Invar have a thermal expansion coefficient close to zero and can be directly used as the base for the invented spectrometer, the base can also be made from a composite material having compensating coefficients of thermal expansion. For example, the composite material can be composed of two materials with one having a positive coefficient of thermal expansion and the other a negative coefficient of thermal expansion. As shown in FIG. 6(*a*), the base 616 can be a metal with a positive coefficient of thermal expansion and the embedded bars 618 can be a different material with a negative coefficient of thermal expansion. Due to the nearly coaxial feature of the diffracted beams with respect to the input beam of the presently invented Littrow spectrometer configuration, an additional advantage of the invention is the possibility to also compensate for any thermally induced variation of the imaging function to the lenses by selecting an opposing thermal expansion coefficient of the base. For example, the focal length of glass lenses tends to change with temperature, which change can be compensated by thermal expansion or contraction of the base.

Still another feature of the present invention to address the stability issue is the use of a rectangular pixel based linear detector array in which the height of the each pixel is selected to cover a wider drift range of the focused spectral line induced by potential vibration or temperature variation. As a result, under most practical conditions, the spectrometer output is stable and meanwhile the size of each pixel of the line scan camera is not too large to markedly affect the performance of the camera in terms of speed and dark noise. A preferred height range of the pixel is, for example, from 10 micron to 500 micron. It should be noted that there is a trade off between the height of the pixels and the performance of the photodetector array. This is because along with the increase in the photosensitive area of each pixel, the speed of the line scan camera may be lowered resulting from increased capacitance and the signal to noise ratio of the detector array may deteriorate due to an increased dark noise.

SD-OCT is described by Leitgeb et al., ("Ultrahigh resolution Fourier domain optical coherence tomography", *Optics Express* 12 10, pp. 2156-2165 (2004)), by Choma and Sarunic ("Sensitivity advantage of swept source and Fourier domain optical coherence tomography." *Optics Express* 11(18): 2183-2189 (2003)), and by de Boer et al. ("Improved signal-to-noise ratio in spectral-domain compared with time-domain optical coherence tomography." *Optics Letters* 28(21): 2067-2069 (2003)). As we have mentioned in the background section, so far, all prior art SD-OCT systems have used two lenses in the spectrometer in which one lens is used for collimating the input beam to propagate towards the grating and the other is used to focus the dispersed spectral beams onto a detector array. A novel feature of the present invention is the incorporation of a spectrometer in an SD-OCT system that uses one or more common shared focusing element(s) for both the input as well as the dispersed output beams.

Figure 9:
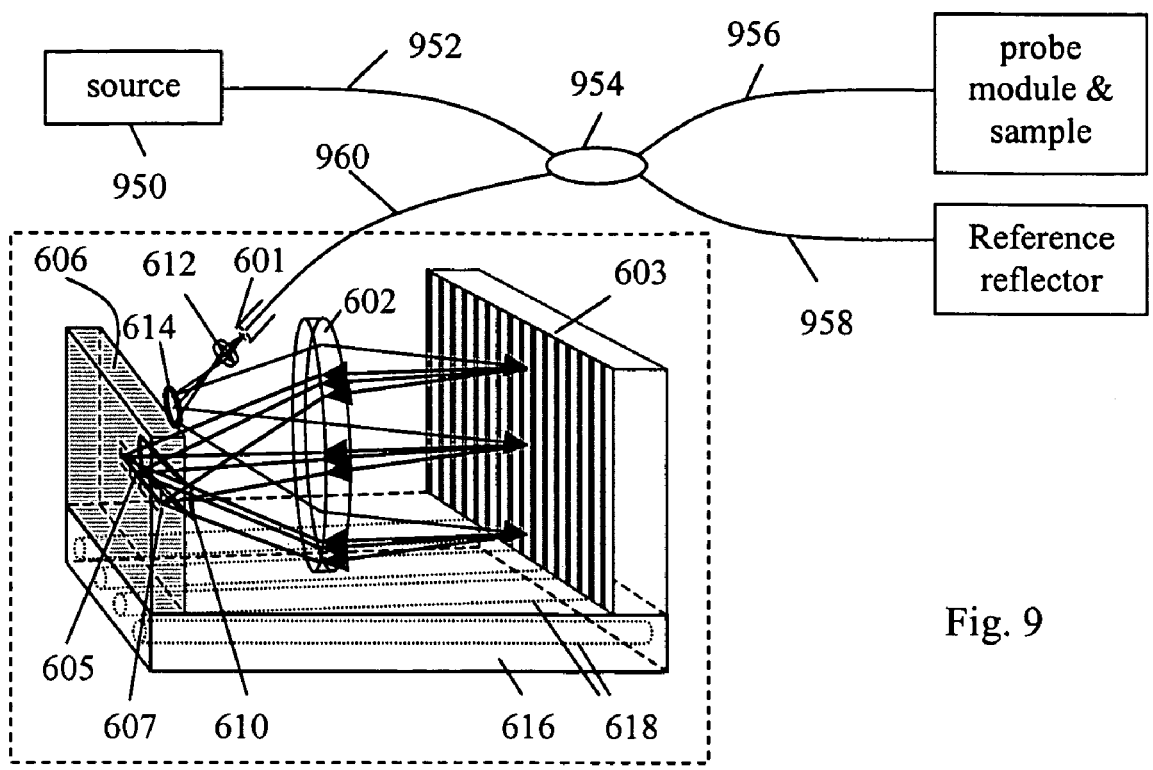
FIG. 9 shows a preferred embodiment of a Littrow spectrometer in an SD-OCT system.

FIG. 9 shows a preferred embodiment of a Littrow spectrometer (as shown in FIG. 6) as used in a spectral domain optical coherence tomography (SD-OCT) system. In this preferred embodiment, light from a broadband source 950 is directed through a single mode fiber 952 to a fiber coupler 954 and is split into the sample arm 956 and the reference arm 958. Light returned from the sample arm 956 interferes with light returned from the reference arm 958. Part of the interfered optical beam is guided by the detection arm 960 and sent to the Littrow spectrometer. The Littrow spectrometer is preferably one that has one or more of the presently invented advantageous features as discussed before. The key advantage of a Littrow spectrometer in an SD-OCT system is its compactness and the stability that can be achieved as a result of the compactness.

A preferred light source for SD-OCT is one with a short coherence length, on the order of 1 to 50 microns. If the center of the source spectrum is 820 nm, a coherence length of 10 microns corresponds to an optical bandwidth of approximately 60 nm, full width at half maximum intensity. It is desirable to collect a spectrum substantially wider than the width of the source, so a reasonable range for the spectrometer would be 770 to 870 nm. Referring to FIG. 3, a grating 303 with 1500 grooves per mm, with an input beam inclined at E=5 degrees from the plane perpendicular to the grooves, is in Littrow configuration for first order diffraction of 820 nm when oriented with an angle of 38.0 degrees between the input beam and the normal to the grating; as follows from equation (3) above with $\alpha=\beta_m$ and the order m set to 1. The range of diffracted beams leave the grating at angles ranging from $\beta$=32.5 degrees from the grating normal for the 770 nm light, to $\beta$=43.5 degrees from the grating normal for the 870 nm light. There are commercially available appropriate line scan cameras or sensors for use at location 305 in FIG. 3 with 2048 pixels spaced at approximately 15 microns, each pixel having a square light-sensitive area 15 microns on a side. Shared lens 302 with focal length 160 mm will focus the diffracted beams such that wavelengths 770 nm to 870 nm are focused on opposite ends of this 30.72-mm-long sensor. Typical input fiber 301 appropriate for this wavelength has an exit numerical aperture near 0.14, so the shared lens 302 will form a collimated input beam approximately 45 mm in diameter. The diffracted beams have substantially the same diameter, which leads to a diffraction limit of 7-microns in diameter for the focal spots on the sensor, these focal spots formed by focusing the diffracted beams with shared lens 302.

The distortion of the line focus depends on the location of the shared lens 302. One can estimate the distortion by tracing the central rays, as depicted in FIG. 2, to a plane whose normal bisects angle between the incident beam and the central diffracted beam, at a distance f=160 mm from the center of the grating. The intersection of the outgoing cone of diffracted rays with this plane has the shape of the hyperbola $z=\tan \epsilon \sqrt{f^2+x^2}$. The sag is 64 microns, the sag being the change in z from the center to the ends of the 30.72 mm long spectrum. Such a distortion of the focused spectrum would spill light from the 15-micron-pixel CCD sensor, unless proper placement of shared lens 302 is used to correct this bend in the focused spectrum.

Refining the arrangement of the previous paragraph as illustrated in FIG. 6, lens 612 can be used to adjust the numerical aperture of the light from fiber 601 so as to adjust the diameter of the collimated beam. The collimated beam diameter may be adjusted for example to allow a grating 603 or shared lens 602 of convenient size, and/or to adjust the diffraction limit on the size of the focused diffracted beams. Field flattening lens 610 is typically specified using numerical modeling of the optical system. The shapes of the refractive surfaces on lens 610 are typically adjusted in conjunction with those on lens 602 to provide an optimally flat image on line scan sensor 610, within certain constraints on the surfaces to allow for inexpensive lens manufacture.

The Fourier transform of the spectral intensities recorded by line sensor 507 or line sensor 607 provides the reflectance distribution along the path of the sample, e.g. along the depth within the sample. The detected reflectance distribution includes not only specular reflections, but also other scattering processes that return light to the spectrometer. Details of the processing steps required to form a high resolution image of the reflectance are known in the art and described by Leitgeb et al., ("Ultrahigh resolution Fourier domain optical coherence tomograph", *Optics Express* 12 10, pp. 2156-2165 (2004)), by Choma and Sarunic ("Sensitivity advantage of swept source and Fourier domain optical coherence tomography." *Optics Express* 11(18): 2183-2189 (2003)), and by deBoer et al. ("Improved signal-to-noise ratio in spectral-domain compared with time-domain optical coherence tomography." *Optics Letters* 28(21): 2067-2069 (2003)).

Note that there may be a large number of variations of the optical interferometer as well as of the Littrow spectrometer in the SD-OCT system. For example, the optical interferometer does not need to be limited to the Michelson type and can be Mach-Zehnder or a combination of Michelson and Mach-Zehnder or others as long as it can split an input beam into at least two beams and recombine some portion of the split beams. The reference arm hence does not need to be restricted to reflective type and can be transmissive (for example, the reference arm can include a loop back to the beam splitter 954). The optical path does not need to be restricted to optical fibers and can be bulk optics based or a combination of fiber optics and bulk optics. Other optical component can be included in the optical path to manipulate the property of the light beam, examples include polarizer(s), polarization controller(s), polarization beam splitter(s), waveplate(s), lens(es), mirror(s), non-polarization beam splitter(s), and so on, in the fiber optics or bulk optics form. Other configurations that have been used for OCT systems include balanced detection scheme (see for example, US20040239938/WO04111929) and high optical power efficiency designs (see for example, U.S. Pat. No. 6,657,727). These can all be combined with the presently invented spectrometer for SD-OCT applications.

The spectrometer in the spectral domain OCT system does not need to be limited to a conical diffraction Littrow spectrometer. It can be a classical in-plane diffraction spectrometer. In addition, the grating does not need to be restricted to a plane grating. The grating can be a curved or concave grating such as an Echelle grating that can serve both the dispersing and the focusing functions. A main feature of the present invention is the use of a spectrometer in an SD-OCT system wherein the spectrometer has one or more shared focusing element(s) for the input and diffracted output beams. The shared focusing element(s) can be a lens or a combination of lenses, or a curved/concave grating or a curved/concave mirror.

Figure 10:
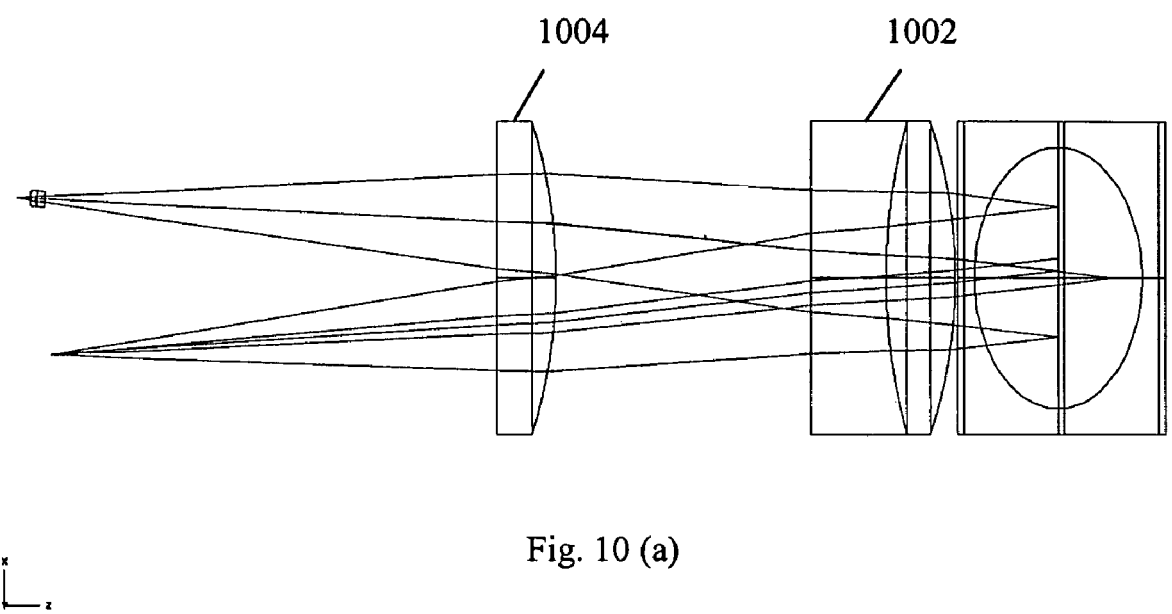
FIG. 10($a$) shows the design of a lens system for a Littrow spectrometer in a SD-OCT system, consisting of a doublet and a singlet, which collectively act as the shared common lens for the input beam and the diffracted output beams.
Figure 10:
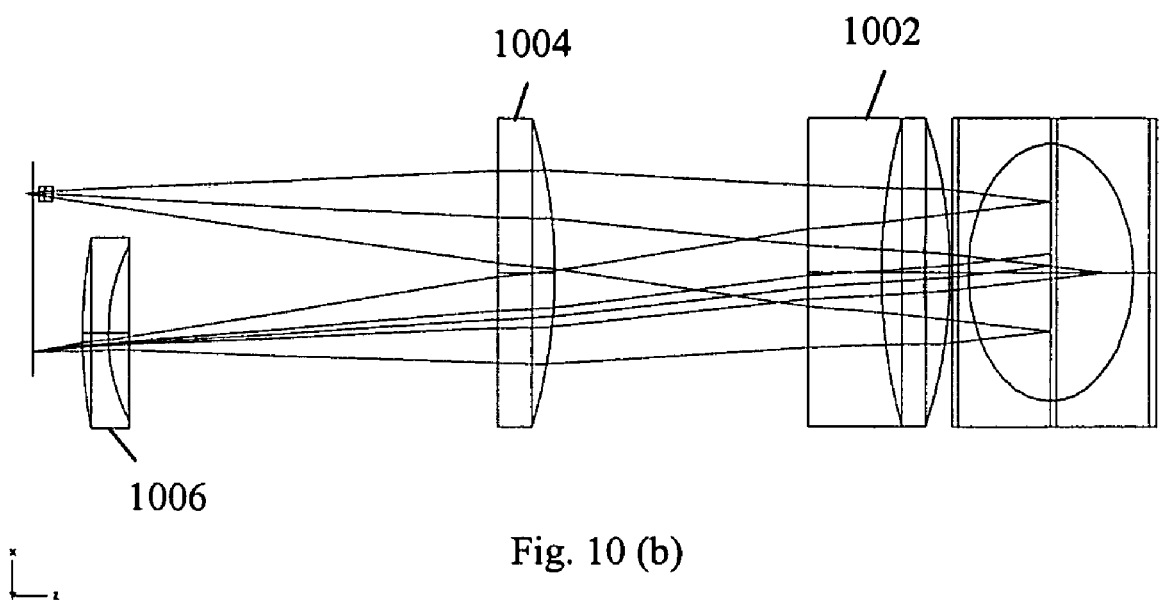

In a preferred embodiment, the spectrometer in the spectral domain OCT system is a conical diffraction Littrow spectrometer with the presently invented advantageous features. FIGS. 10(a) and (b) show a preferred embodiment of a lens design within the spectrometer that can compensate for the distortion introduced by conical diffraction. FIG. 10(a) shows the design of a lens system for a Littrow spectrometer in an SD-OCT system, consisting of a doublet 1002 and a singlet 1004, which collectively act as the shared common lens for the input beam and the diffracted output beams. The doublet 1002 is a combination of two lenses made of crown and flint glasses. The designed lens system has an effective focal length of 130 mm. The computer models a broadband light beam with a center wavelength of about 840 nm and a spectral width from 795 nm to 885 nm sent to a 1500 groove/mm grating that is tipped with a tip angle of about 5 degrees to enable conical diffraction and the diffracted beams are focused onto a 30 mm wide pixel array of a line scan or CCD camera. The set of lenses in the model depicted in FIG. 10(a) have negative (barrel) distortion that causes the focused spectral line to curve up, opposite the situation shown in inset portion of FIG. 3a, with the ends of the spectrum now 15 microns above the center. FIG. 10(b) shows that with the insertion and appropriate placement of a field flattening lens 1006 that has an approximately 3.1% positive (pincushion) distortion at the ends of the CCD sensor, the focused spectral line can be straightened to have only a maximum of 1 micron deviation from a straight line.

Alternatively, a common lens can be shared in front of the grating by both the input and output arms and in addition, the shared lens can have a certain distortion that substantially compensates for the distortion introduced to the diffracted spectral beams by conical diffraction. Additional optical components can be placed in either the input or output or both arms to provide additional functions. For example, a field flattening lens can be placed in the output arm to further straighten the focused spectral line. A vertically high focusing power cylindrical lens can be substantially rigidly mounted on the camera in front of the pixel array to further reduce the focused spectral line height in the vertical direction to render the spectrometer output more stable. Alternatively, a vertically de-magnifying light pipe array can be used with its smaller size end aligned with the pixel array and rigidly mounted on the line scan camera, and its large size end arranged to receive the focused spectral line. A beam folding mirror can be arranged in the input arm to enable the acceptance of the input light beam from the front side of the camera. An input lens can also be used to function for numerical aperture matching. The detector array can be a one dimensional line scan camera or a two dimensional area scan camera or an area sensor with one line used. For SD-OCT applications, a high data rate of the detector array (preferably greater than 1000 lines per second) is preferably desired, which is quite different from that of a conventional array spectrometer that uses an ordinary CCD with a typical integration time of 20 to 5000 ms.

Another issue not fully addressed by previous SD-OCT designs is the polarization dependence of the spectrometer. A standard grating is generally more efficient for one polarization state than for the orthogonal polarization state. As can be seen from a US patent application (US20040239943) and a pending U.S. patent application (Ser. No. 10/811,748), one approach to solve the problem is to select only one polarization direction of the interfered beam and to launch the linearly polarized beam into the spectrometer with a selected orientation. Another approach is to separate the interfered beam into two perpendicular polarizations such that two linearly polarized interfered beams can be sent to two spectrometers. The former approach may result in a reduced signal to noise ratio and the latter approach requires two spectrometers which will substantially increase the cost of the system.

The input to the spectrometer in an SD-OCT will typically have varying polarization state, unless measures are taken to control the polarization. In OCT it is advantageous to ensure a high value of the modulation depth of the interfered beam by adjusting the polarization state of either the reference arm or the sample arm or both arms in the interferometer so that the polarizations of the two beams are substantially matched. This adjustment is commonly done individually for each sample to be measured, so as to compensate for rotation of the polarization in the sample, and for rotation of polarization in the optics leading to the sample, possibly including optical fiber. One could also adjust the polarization state of the interfered beam in the detection arm of the interferometer so that the final state of polarization of the interfered beam shining onto the grating in the spectrometer is substantially the polarization state for which the grating has higher diffraction efficiency. However, in fiber interferometers commonly used for OCT, the final polarization state depends upon the bending of the optical fiber in any arm of the interferometer, which may change as a function of temperature and mechanical vibration, so it may be necessary to employ dynamic controlling of the polarization state in a fiber. This obviously will add cost to an SD-OCT system.

If the spectrometer is substantially polarization-independent, then the SD-OCT system need only substantially match the polarization states between sample and reference arms, sending the interfered beam to the spectrometer with no further polarization control. A substantially polarization-independent spectrometer is advantageous in the design of a simple and reliable SD-OCT system.

Figure 11:
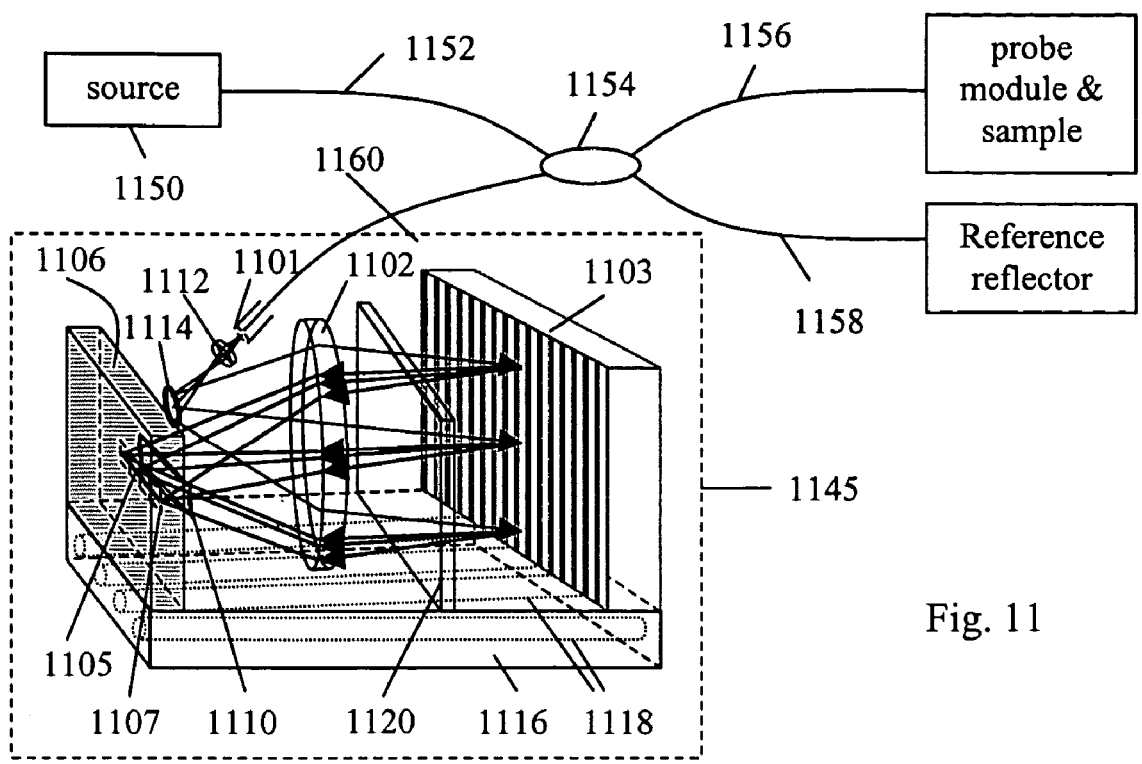
FIG. 11 shows a Littrow spectrometer in an SD-OCT system in which a polarization compensation element is inserted in the spectrometer to render it substantially polarization independent.

As one aspect of the invention, the Littrow spectrometer in an SD-OCT system is made substantially polarization independent. A first simple way is to select a proper blaze angle and a proper grating groove density such that the diffraction efficiency for the mutually orthogonal S and P polarization cross with each other, i.e. is substantially equal, for the central wavelength of interest. A second simple way to compensate for the polarization dependence is to insert a polarization compensating optical element 1120 in either the input or the output arm or both arms of the spectrometer as shown in FIG. 11. Such a polarization compensator 1120 can be a partial polarizer so that while light in one polarization direction is substantially transmitted, light in the orthogonal polarization direction is partially absorbed or reflected away from the spectrometer. There may be many partial polarizers and a good example is a single piece or a stacked multiple pieces of glass tilted around the Brewster angle.

Figure 12:
FIG. 12($a$) shows a grating with a surface relief profile that has two different grating elements of the same grating period but different modulation depth or blaze angles to render the grating substantially polarization independent FIG. 12($b$) shows a hybrid metallic-dielectric grating that has a metallic base layer and layers of dielectric materials of varying refractive index to render the grating substantially polarization independent FIG. 12($c$) shows a lamellar volume grating that has an approximately rectangular grating profile with a height-to-width ratio of the grooves greater than two to render the grating substantially polarization independent
Figure 12:
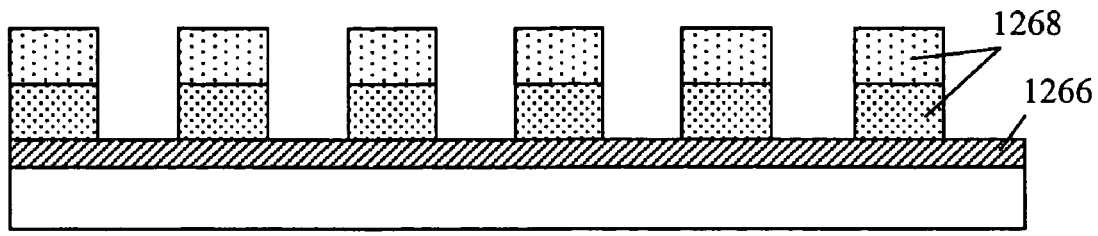
Figure 12:
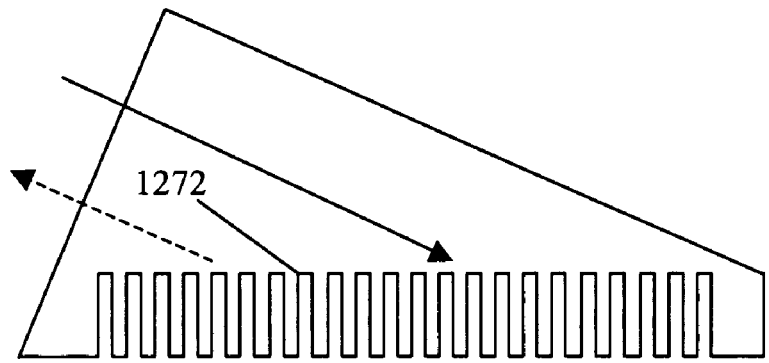
Figure 12:
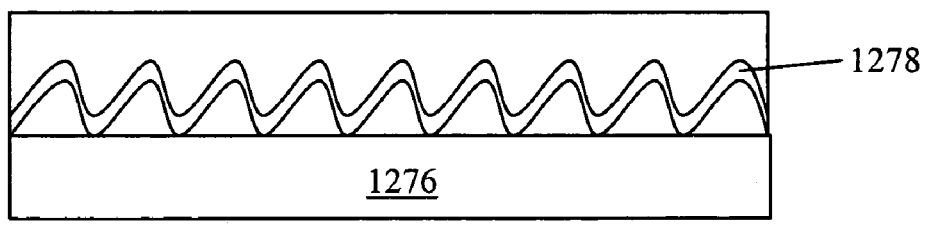
Figure 12:
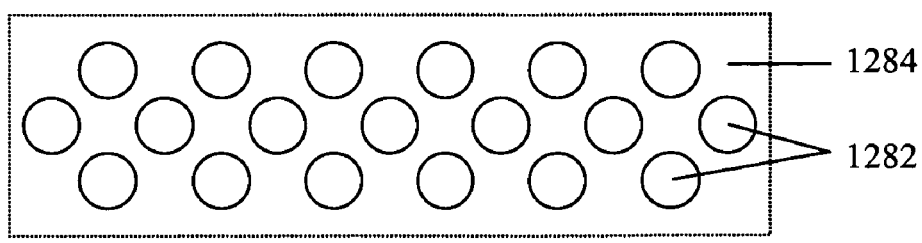

Alternatively, the grating in the spectrometer can be made substantially polarization independent in various ways as shown in FIG. 12(a) to (e). A first example is a grating with a surface relief profile that has two different grating elements 1260 and 1262 of the same grating period but different modulation depth or blaze angles to render the grating substantially polarization independent (see for example, U.S. Pat. No. 6,487,019) as shown in FIG. 12(a). Note that the number of repeating surface relief profiles in each grating element 1260 or 1262 can vary from 1 to N, where N is an integer. A second example is a hybrid metallic-dielectric grating that has a metallic base layer 1266 and layers of dielectric materials of varying refractive index 1268 to render the grating substantially polarization independent (see for example, U.S. Pat. No. 6,754,006) as shown in FIG. 12(b). A third example is a lamellar volume grating that has an approximately rectangular grating profile 1272 with a height-to-width ratio of the grooves greater than two to render the grating substantially polarization independent (see for example, U.S. Pat. No. 6,724,533) as shown in FIG. 12(c). A fourth example is a grating with a substrate 1276 and a reflective material 1278 adjacent the substrate 1276 to render the grating substantially polarization independent (see for example, U.S. Pat. No. 6,577,786) as shown in FIG. 12(d). Another example is a blazed photonic crystal grating made with embedded circular rods 1282 in another optical medium 1284 that has a high diffraction efficiency and a high degree of polarization independence (see for example, Popov E. et al. "Almost perfect blazing by photonic crystal rod gratings", Applied Optics 40(15) 2417-2422) as shown in FIG. 12(d)

It should be understood that the presently invented apparatus(es) can also be extended to the associated methods. For example, one aspect of the invention is a method of focusing a conically diffracted spectrum substantially into a line, comprising the step of compensating the conical diffraction induced distortion to the spectrally dispersed beams. More preferably, the distortion compensation is achieved by placing an aberrant lens in front of the grating in such a way that the distortion of the lens substantially compensates for the distortion introduced to the dispersed spectrum by the conical diffraction. Another aspect of the invention is a method of performing spectral domain optical coherence tomography, comprising the steps of sending the interfered beam from an interferometer to a Littrow spectrometer for spectral interferogram information extraction. Still another aspect of the invention is a method of performing spectral domain optical coherence tomography, comprising the steps of sending the interfered beam from an interferometer to a polarization independent spectrometer for spectral interferogram information extraction.

It should be noted that the presently invented Littrow spectrometer should not be limited to the application in SD-OCT. On the contrary, the spectrometer can be used for any application that requires spectral analysis of optical radiation. A main application is in spectroscopy including astronomical spectroscopy, atomic absorption spectroscopy, luminescence spectroscopy, fluorescence spectroscopy, total internal reflection spectroscopy, and Raman spectroscopy. Furthermore, the presently invented Littrow spectrometer can also be used for optical coherence domain ranging for distance measurement.

The foregoing description of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

The following patents, patent applications and other documents are hereby incorporated by reference.

US PATENT DOCUMENTS

U.S. Pat. No. 5,565,986
U.S. Pat. No. 6,487,019
U.S. Pat. No. 6,577,786
U.S. Pat. No. 6,657,727
U.S. Pat. No. 6,710,330
U.S. Pat. No. 6,724,533
U.S. Pat. No. 6,754,006
U.S. Pat. No. 6,757,113

U.S. Pat. No. 6,847,454
U.S. Pat. No. 6,859,317
US20040239938
US20040239943
US20050018201
U.S. patent application, Ser. No. 10/811,748

FOREIGN PATENT DOCUMENTS

JP2000-046729
JP2001-174404
WO03062802
2 476 174
WO04111929
WO2004043245
WO2004111929

OTHER PUBLICATIONS

De-Boer, J. F., et al. (2003). "Improved signal-to-noise ratio in spectral-domain compared with time-domain optical coherence tomography." *Optics Letters* 28(21): 2067-2069

Choma, M. A., M. V. Sarunic, et al. (2003). "Sensitivity advantage of swept source and Fourier domain optical coherence tomography." *Optics Express* 11(18): 2183-2189

Leitgeb, R. A., et al. (2003). "Phase-shifting algorithm to achieve high-speed long-depth-range probing by frequency-domain optical coherence tomography." *Optics Letters* 28(22): 2201-2203

Leitgeb, R. A., et al. (2003). "Performance of Fourier domain vs. time domain optical coherence tomography." *Optics Express* 11(8): 889-894

Maystre D. et al. (1985) "Geometrical invariance property of gratings" Applied Optics 24(2): 215-216

Popov E. et al. "Almost perfect blazing by photonic crystal rod gratings", Applied Optics 40(15) 2417-2422

Smith, L. M. and C. C. Dobson (1989). "Absolute displacement measurements using modulation of the spectrum of white light in a Michelson interferometer." *Applied Optics* 28(15): 3339-3342

Wojtkowski, M., et al. (2003). "Real-time in vivo imaging by high-speed spectral optical coherence tomography." *Optics Letters* 28(19): 1745-1747

Zeylikovich, I. et al. (1998). "Nonmechanical grating-generated scanning coherence microscopy." *Optics Letters* 23(23): 1797-1799

We claim:

1. A spectrometer for monitoring the magnitude of a broadband light beam as a function of wavelength comprising:
    a grating for angularly dispersing an incident light beam as a function of wavelength;
    a linear detector array for receiving and monitoring the dispersed light beam, with the incident beam, the grating and the detector array being positioned in a substantially Littrow condition and with the grating being tipped with respect to the incoming beam to induce conical diffraction to thereby spatially separate the path of the diffracted beam from the incident beam, with said conical diffraction resulting in the footprint of the dispersed light having a non-linearity in a direction perpendicular to the axis of the array; and
    a first optical element located between the grating and the array for reducing the non-linearity caused by the conical diffraction so the registration of the footprint with the array is improved.

2. A spectrometer as recited in claim 1, wherein the first optical element is located in the path of both the incident beam and the diffracted beam.

3. A spectrometer as recited in claim 1, further including a second optical element located between the grating and the array to spatially flatten the focal points of the dispersed light across the wavelength range in the plane of the array to improve the alignment with the array.

4. A spectrometer as recited in claim 3, wherein the second optical element is a meniscus lens.

5. A spectrometer as recited in claim 3, wherein the function of the first and second optical elements are combined into a single lens.

6. A spectrometer as recited in claim 1, wherein said grating is curved.

7. A spectrometer as recited in claim 1, further comprising an optical fiber having an output end for delivering the light beam to the spectrometer.

8. A spectrometer as recited in claim 7, further including a lens positioned near the output end of the fiber to adjust the numerical aperture of the light exiting the fiber and entering the spectrometer.

9. A spectrometer as recited in claim 7, further comprising a folding mirror for directing the light exiting the fiber towards the grating.

10. A spectrometer as recited in claim 1, wherein said grating and said array are operatively coupled to a mount having a low coefficient of thermal expansion.

11. A spectrometer as recited in claim 1, wherein said grating and said array are operatively coupled to a mount having a coefficient of thermal expansion which compensates for thermally induced variations of the imaging functions of said optical element.

12. A spectrometer as recited in claim 1, further comprising a first cylindrical lens rigidly mounted to and aligned with the detector array.

13. A spectrometer as recited in claim 12, further comprising a separate, second cylindrical lens for correcting the astigmatism created by the first cylindrical lens.

14. A spectrometer as recited in claim 1, further comprising a vertically demagnifying light pipe with the de-magnified end of the light pipe being rigidly mounted to and aligned with the detector array and the opposing end of the light pipe being positioned to receive light diffracted from the grating.

15. A spectrometer as recited in claim 1, coupled to a spectral domain optical coherence tomography (OCT) system with the output of the spectrometer being used to evaluate a sample.

16. A spectrometer as recited in claim 1, wherein the detector array is a line scan camera.

17. A spectrometer as recited in claim 16, wherein the line scan camera has a data rate of greater than 1000 lines per second.

18. A spectrometer as recited in claim 1, wherein the detector array is a 2D area scan camera.

19. A spectrometer as recited in claim 1, configured to generate an output that is substantially insensitive to the polarization state of the incoming beam.

20. A spectrometer for monitoring the magnitude of a broadband light beam as a function of wavelength comprising:
    a grating for angularly dispersing an incident light beam as a function of wavelength;
    a linear detector array for receiving and monitoring the dispersed light beam and with the grating being tipped with respect to the incident beam to induce conical diffraction to thereby spatially separate the path of the diffracted beam from the incident beam, with said conical diffraction resulting in the footprint of the dispersed light having a non-linearity in a direction perpendicular to the axis of the array; and a first optical element located between the grating and the array and in the path of both the incident and the diffracted beam, said optical element for modifying the focus of the beam and for reducing the non-linearity caused by the conical diffraction so the registration of the footprint with the array is improved.

21. A spectrometer as recited in claim 20, wherein the incident beam, the grating and the detector array are positioned in a substantially Littrow condition.

22. A spectrometer as recited in claim 20, further including a second optical element located between the grating and the array to spatially flatten the focal points of the dispersed light across the wavelength range in the plane of the array to improve the alignment with the array.

23. A spectrometer as recited in claim 22, wherein the second optical element is a meniscus lens.

24. A spectrometer as recited in claim 20, coupled to a spectral domain optical coherence tomography (OCT) system with the output of the spectrometer being used to evaluate a sample.

25. A spectrometer as recited in claim 24, wherein the detector array is a line scan camera.

26. A spectrometer for monitoring the magnitude of a broadband light beam as a function of wavelength comprising:

a grating for angularly dispersing an incident light beam as a function of wavelength;

a linear detector array for receiving and monitoring the dispersed light beam, with the incident beam, the grating and the detector array being positioned in a substantially Littrow condition and with the grating being tipped with respect to the incoming beam to induce conical diffraction to thereby spatially separate the path of the diffracted beam from the incident beam, with said conical diffraction resulting in the footprint of the dispersed light having a non-linearity in a direction perpendicular to the axis of the array; and means for reducing the non-linearity caused by the conical diffraction so the registration of the footprint with the array is improved.

27. A spectrometer as recited in claim 26, wherein said grating is an Echelle grating having a curvature for focusing the dispersed beam and wherein said means includes said Echelle grating.

28. A spectrometer as recited in claim 26, wherein said means includes a plurality of lenses located between the grating and the array to reduce the non-linearity caused by the conical diffraction so the registration of the footprint with the array is improved and for spatially flattening the focal points of the dispersed light across the wavelength range in the plane of the array to improve the alignment with the array.

29. A spectral domain optical coherence tomography (OCT) system comprising:

a broadband light source;

a beam splitter for dividing the light along a sample and a reference path;

a spectrometer for receiving light returned from both the sample and the reference paths, said spectrometer including a grating for angularly dispersing the light as a function of wavelength and a linear detector array for receiving and monitoring the dispersed light and with the path of the received light, the grating and the detector array being positioned in a substantially Littrow condition, and wherein the grating is tipped with respect to the received light to induce conical diffraction to thereby spatially separate the path of the dispersed light from the incident light with said conical diffraction resulting in the footprint of the dispersed light having a non-linearity in a direction perpendicular to the axis of the array and further including a means for reducing said non-linearities, said spectrometer for generating output signals as a function of wavelength;

a processor for analyzing the output signals to derive a reflectance distribution along the sample path;

an optical fiber having an output end for delivering the light to the spectrometer; and a lens positioned near the output end of the fiber to adjust the numerical aperture of the light exiting the fiber and entering the spectrometer.

30. An OCT system as recited in claim 29, wherein a common focusing optic is located in the path of both the received light and the dispersed light.

31. An OCT system as recited in claim 29, wherein said beam splitter which divides the light along the sample and reference paths also functions to combine the light returned from both the sample and the reference paths.

32. A spectral domain optical coherence tomography (OCT) system comprising:

a broadband light source;

a beam splitter for dividing the light along a sample and a reference path;

a spectrometer for receiving light returned from both the sample and the reference paths, said spectrometer including a grating for angularly dispersing the light as a function of wavelength and a linear detector array for receiving and monitoring the dispersed light and with the path of the received light, the grating and the detector array being positioned in a substantially Littrow condition, and wherein the grating is tipped with respect to the received light to induce conical diffraction to thereby spatially separate the path of the dispersed light from the incident light, with said conical diffraction resulting in the footprint of the dispersed light having a non-linearity in a direction perpendicular to the axis of the array, said spectrometer further including an optical element located between the grating and the array and in the path of both the received light and the dispersed light, said optical element for modifying the focus of the beam and for reducing the non-linearity caused by the conical diffraction so the registration of the footprint with the array is improved, said spectrometer for generating output signals as a function of wavelength; and a processor for analyzing the output signals to derive a reflectance distribution along the sample path.

33. An OCT system as recited in claim 32, wherein said beam splitter which divides the light along the sample and reference paths also functions to combine the light returned from both the sample and the reference paths.

34. An OCT system as recited in claim 32, further including a second optical element located between the grating and the array to spatially flatten the focal points of the dispersed light across the wavelength range in the plane of the array to improve the alignment with the array.

35. An OCT system as recited in claim 34, wherein the second optical element is a meniscus lens.

36. An OCT system as recited in claim 32, further comprising an optical fiber having an output end for delivering the light beam to the spectrometer.

37. An OCT system as recited in claim 36, further including a lens positioned near the output end of the fiber to adjust the numerical aperture of the light exiting the fiber and entering the spectrometer.

38. An OCT system as recited in claim 32, wherein said grating and said array are operatively coupled to a mount having a low coefficient of thermal expansion.

39. An OCT system as recited in claim 32, wherein said grating and said array are operatively coupled to a mount having a coefficient of thermal expansion which compensates for thermally induced variations of the imaging functions of said optical element.

40. An OCT system as recited in claim 32, further comprising a first cylindrical lens rigidly mounted to and aligned with the detector array.

41. An OCT system as recited in claim 40, further comprising a separate, second cylindrical lens for correcting the astigmatism created by the first cylindrical lens.

42. An OCT system as recited in claim 32, further comprising a vertically demagnifying light pipe with the de-magnified end of the light pipe being rigidly mounted to and aligned with the detector array and the opposing end of the light pipe being positioned to receive light diffracted from the grating.

43. An OCT system as recited in claim 32, wherein the detector array is a line scan camera.

44. An OCT system as recited in claim 43, wherein the line scan camera has a data rate of greater than 1000 lines per second.

45. An OCT system as recited in claim 32, wherein the detector array is a 2D area scan camera.

46. An OCT system recited in claim 32, wherein the spectrometer is configured to generate an output that is substantially insensitive to the polarization state of the incoming beam.

47. A spectral domain optical coherence tomography (OCT) system comprising:
   a broadband light source;
   a beam splitter for dividing the light along a sample and a reference path;
   a spectrometer for receiving light returned from both the sample and the reference paths, said spectrometer including a grating for angularly dispersing the light as a function of wavelength and a linear detector array for receiving and monitoring the dispersed light and with the path of the received light, the grating and the detector array being positioned in a substantially Littrow condition, said spectrometer further including a first cylindrical lens rigidly mounted to and aligned with the detector array and a separate, second cylindrical lens for correcting the astigmatism created by the first cylindrical lens, said spectrometer for generating output signals as a function of wavelength; and
   a processor for analyzing the output signals to derive a reflectance distribution along the sample path.

48. A spectral domain optical coherence tomography (OCT) system comprising:
   a broadband light source;
   a beam splitter for dividing the light along a sample and a reference path;
   a spectrometer for receiving light returned from both the sample and the reference paths, said spectrometer including a grating for angularly dispersing the light as a function of wavelength and a linear detector array for receiving and monitoring the dispersed light and with the path of the received light, the grating and the detector array being positioned in a substantially Littrow condition, said spectrometer further including a vertically demagnifying light pipe with the de-magnified end of the light pipe being rigidly mounted to and aligned with the detector array and the opposing end of the light pipe being positioned to receive light diffracted from the grating, said spectrometer for generating output signals as a function of wavelength; and
   a processor for analyzing the output signals to derive a reflectance distribution along the sample path.

49. An OCT system as recited in claim 29, wherein said means for reducing non-linearities is an optical element located between the grating and the array.

50. A spectral domain optical coherence tomography (OCT) system comprising:
   a broadband light source;
   a beam splitter for dividing the light along a sample and a reference path;
   a spectrometer for receiving light returned from both the sample and the reference paths, said spectrometer including a grating for angularly dispersing the light as a function of wavelength and a linear detector array for receiving and monitoring the dispersed light and with the path of the received light, the grating and the detector array being positioned in a substantially Littrow condition, and wherein the grating is tipped with respect to the received light to induce conical diffraction to thereby spatially separate the path of the dispersed light from the incident light with said conical diffraction resulting in the footprint of the dispersed light having a non-linearity in a direction perpendicular to the axis of the array and further including a means for reducing said non-linearities, said spectrometer for generating output signals as a function of wavelength; and
   a processor for analyzing the output signals to derive a reflectance distribution along the sample path.

51. An OCT system as recited in claim 50, wherein said means for reducing non-linearities is an optical element located between the grating and the array.

* * * * *